US 12,303,308 B2

(12) United States Patent
Tomaru et al.

(10) Patent No.: US 12,303,308 B2
(45) Date of Patent: May 20, 2025

(54) X-RAY DIAGNOSIS APPARATUS AND NON-TRANSITORY COMPUTER READABLE STORAGE MEDIUM

(71) Applicant: CANON MEDICAL SYSTEMS CORPORATION, Otawara (JP)

(72) Inventors: Takehito Tomaru, Otawara (JP); Haruki Iwai, Otawara (JP); Naoki Yamada, Utsunomiya (JP); Takanori Soutome, Nasushiobara (JP); Takahiro Kuroki, Nasushiobara (JP); Naoya Fujita, Otawara (JP); Hiroki Tonotsuka, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 249 days.

(21) Appl. No.: 18/058,797

(22) Filed: Nov. 25, 2022

(65) Prior Publication Data

US 2023/0165553 A1 Jun. 1, 2023

(30) Foreign Application Priority Data

Nov. 26, 2021 (JP) ................................. 2021-192498

(51) Int. Cl.
*A61B 6/00* (2024.01)
(52) U.S. Cl.
CPC .......... *A61B 6/4452* (2013.01); *A61B 6/4494* (2013.01); *A61B 6/547* (2013.01); *A61B 6/4405* (2013.01)

(58) Field of Classification Search
CPC ............................... A61B 6/547; A61B 6/587
See application file for complete search history.

(56) References Cited

U.S. PATENT DOCUMENTS

| 10,506,995 B2 | 12/2019 | Ninomiya et al. |
| 2017/0172536 A1* | 6/2017 | Song ..................... A61B 6/583 |
| 2017/0360386 A1 | 12/2017 | Ninomiya et al. |

FOREIGN PATENT DOCUMENTS

| JP | 2010-119485 A | 6/2010 |
| JP | 2014-121453 A | 7/2014 |
| JP | 2015-77251 A | 4/2015 |
| JP | 2016-178993 A | 10/2016 |

* cited by examiner

*Primary Examiner* — Dani Fox
(74) *Attorney, Agent, or Firm* — Oblon, McClelland, Maier & Neustadt, L.L.P.

(57) ABSTRACT

An X-ray diagnosis apparatus according to the present embodiment comprises: an X-ray irradiator configured to irradiate X-rays; an imager configured to image an identifier that identifies a position of an X-ray detector which detects X-rays; and processing circuitry configured to calculate, based on the identifier shown on an image imaged by the imager, a relative position of the X-ray irradiator regarding the X-ray detector and an irradiation position of the X-ray irradiator where a corresponding relative position meets a predetermined X-ray imaging condition; and output, based on the relative position and the irradiation position, a movement information of the X-ray irradiator.

10 Claims, 13 Drawing Sheets

MOVEMENT ROUTE LIST LT1

| MOVABLE DIRECTION | PRIORITY | ROUTE 1 | ROUTE 2 | ROUTE 3 |
|---|---|---|---|---|
| ARM EXTENSION AND CONTRACTION | 1 | -5 | 0 | -3 |
| ARM'S VERTICAL MOVEMENT | 2 | -2 | -2 | 0 |
| ARM ROTATION | 3 | 0 | 0 | −45° |
| BODY MOVEMENT | 4 | 0 | -5 | 0 |

X-RAY DIAGNOSIS APPARATUS AND NON-TRANSITORY COMPUTER READABLE STORAGE MEDIUM

CROSS REFERENCE TO RELATED APPLICATIONS

This application is based upon and claims the benefit of priority from the prior Japanese Patent Application No. 2021-192498, filed on Nov. 26, 2021, the entire contents of which are incorporated herein by reference.

FIELD

Embodiments described in the present specification and drawings relate generally to an X-ray diagnosis apparatus and a non-transitory computer readable storage medium.

BACKGROUND

Conventionally, a mobile X-ray diagnosis apparatus that may be moved to a hospital room to perform X-ray imaging is known. Such mobile X-ray diagnosis apparatus, for instance, is used for X-ray fluoroscopy or radiography (hereinafter, generically referred to as X-ray imaging) for subjects that is laid on a bed of the hospital room and not able to move easily, such as during intravenous infusion being bedridden.

Typically, for the mobile X-ray diagnosis apparatus, an X-ray tube which radiates X-rays and an X-ray detector which detects the X-ray may be arranged independently of each other. When using such mobile X-ray diagnosis apparatus for X-ray imaging for the subject that is laid on the bed, an operator loads the X-ray detector between the subject and the bed, moves the X-ray tube, and performs a positioning (aligning) of the X-ray tube and the X-ray detector. Then, the operator, by moving the X-ray tube to an appropriate position relative to the X-ray detector, performs an alignment to obtain an appropriate setting of an X-ray field relative to an X-ray detection surface of the X-ray detector. When appropriate alignment setting is not made, the X-ray will be radiated outside a range of the X-ray detector, unable to image a necessary X-ray image. For this reason, the operator must move the X-ray tube to the appropriate position relative to the X-ray detector when performing X-ray imaging.

However, since all or many parts of the X-ray detector loaded between the subject and the bed are hidden by the subject, the operator has to move the X-ray tube to the position of the X-ray detector which the operator visually presumes. For this reason, there is a problem that it is difficult for the operator to move the X-ray tube to the appropriate position relative to the X-ray detector. Likewise, this problem not only occurs to the mobile X-ray diagnosis apparatus, but also similarly occurs to other types of X-ray diagnosis apparatus where the X-ray detector may be independently arranged against the X-ray tube, such as typical X-ray diagnosis apparatus or portable X-ray diagnosis apparatus. For this reason, for X-ray diagnosis apparatus where the X-ray tube may be independently arranged against the X-ray detector, it is desirable to perform X-ray imaging by moving the X-ray tube to the appropriate position relative to the X-ray detector.

DETAILED DESCRIPTION

With reference to the drawings below, embodiments of an X-ray diagnosis apparatus will be described. Note that, in the description below, same reference signs are given for components substantially identical in terms of configuration and function, and duplicate description will be given only when necessary.

Figure 1:
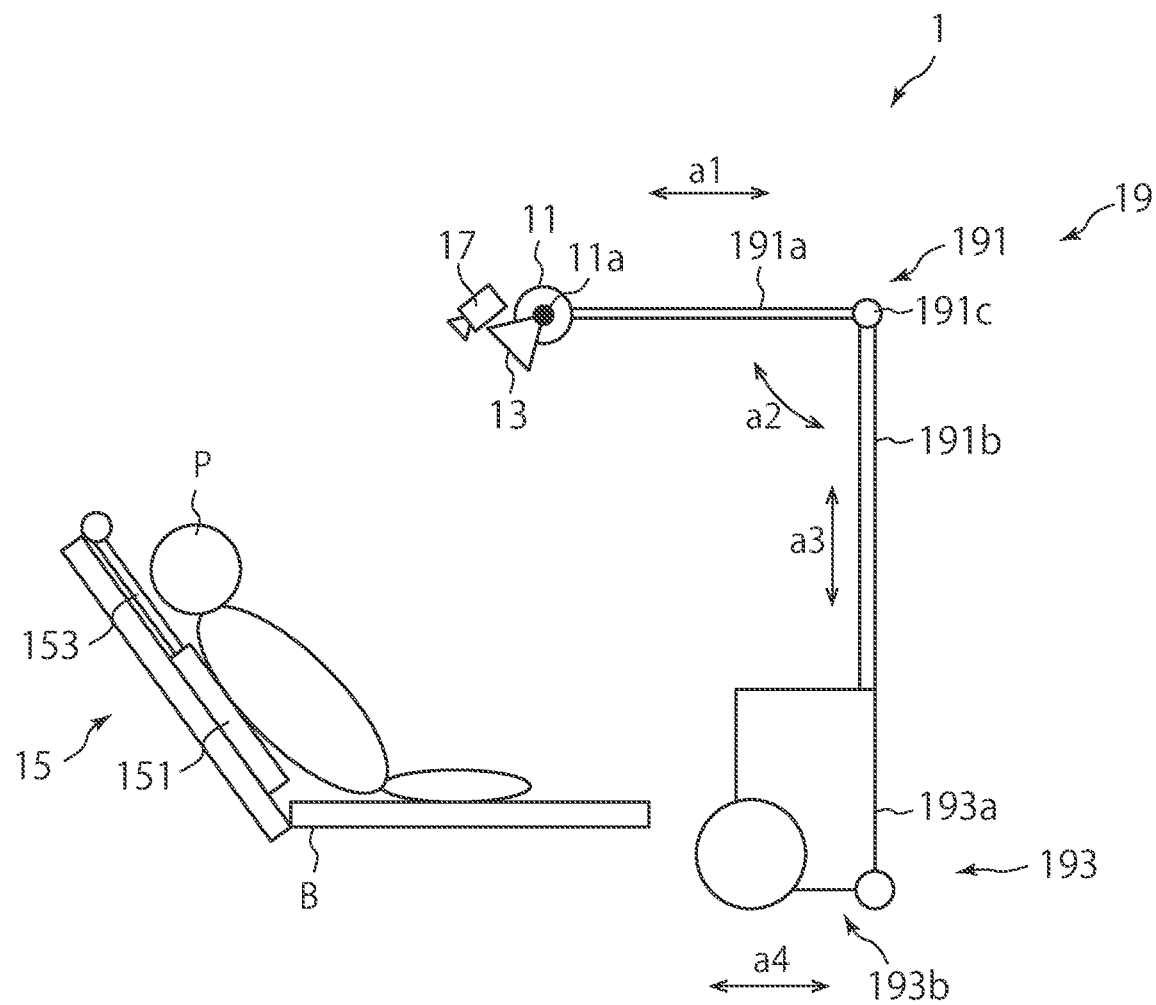
FIG. 1 is a schematic diagram illustrating an exterior of an X-ray diagnosis apparatus according to one embodiment.

FIG. 1 is a schematic diagram illustrating an exterior of an X-ray diagnosis apparatus 1 according to a present embodiment. The X-ray diagnosis apparatus 1 illustrated in FIG. 1, for instance, is a mobile X-ray diagnosis apparatus. Note that the X-ray diagnosis apparatus 1 according to the present embodiment is not limited to the mobile X-ray diagnosis apparatus, and for example, may be realized by an X-ray diagnosis apparatus of an arbitrary type, such as a typical X-ray diagnosis apparatus or a portable X-ray diagnosis apparatus. The present embodiment will be described below with a premise of performing X-ray imaging using the mobile X-ray diagnosis apparatus.

As shown in FIG. 1, the X-ray diagnosis apparatus 1 according to the present embodiment comprises an X-ray tube 11, an X-ray aperture 13, an X-ray detection unit 15, an imager 17, and a support member 19.

The X-ray tube 11, based on a tube current supplied by a high voltage generation circuit and a tube voltage applied by the high voltage generation circuit, generates an X-ray from a focus of the X-ray (hereafter referred to as a tube focus). The position of generating this X-ray is a tube focus position 11a. The X-ray generated at the tube focus is irradiated to an irradiation range restricted by the X-ray aperture 13. The X-ray tube 11, for instance, is provided on a tip of the support member 19. The X-ray tube 11 is connected to the high voltage generation circuit via a high voltage cable provided on the support member 19. Note that the X-ray tube 11 is an example of an X-ray irradiator according to the present embodiment.

The X-ray aperture 13, according to an operation by an operator, restricts the irradiation range of the X-ray. Specifically, the X-ray aperture 13, in order to evade unnecessary exposure outside an imaging site which the operator desires, restricts the irradiation range of the X-ray generated at the tube focus in response to an irradiation area to irradiate the X-ray on a body surface of a subject P. Note that the X-ray aperture 13 is sometimes called as a collimator.

Furthermore, the X-ray aperture 13, with a purpose of reducing an exposure amount on the subject P and enhancing image quality, may have a plurality of predefined filters (hereinafter referred to as a radiation quality adjusting filter). The plurality of radiation quality adjusting filters may be respectively configured with different materials and have a same thickness. The radiation quality adjusting filters are changed the radiation quality of the X-ray generated at the tube focus in response to a thickness. The radiation quality adjusting filter, for instance, is configured by aluminum, copper, etc.

The X-ray detector unit 15 detects the X-ray irradiated by the X-ray tube 11 which penetrated the subject P. The X-ray detection unit 15 is a portable detection unit which may be independently arranged with the X-ray tube 11. The X-ray detection unit 15 is loaded by the operator between the subject P and the bed B. The X-ray detection unit 15 according to the present embodiment comprises an X-ray detector 151 which detects the X-ray that penetrated the subject P and a feature member 153 extended on the X-ray detector 151.

The X-ray detector 151, for instance, is realized by a Flat Panel Detector (hereinafter referred to as an FPD). The FPD has a plurality of semiconductor detection elements arranged in 2D. Each semiconductor detection element detects the X-ray irradiated by the X-ray tube 11 which penetrated the subject P and converts the detected X-ray into electrical signal. The electrical signal generated in each semiconductor detection element is output to an Analog to Digital converter (hereinafter referred to as an A/D converter). The A/D converter converts electrical signal into digital data. The A/D converter generates the digital data. The generated digital data is output to an image generation circuit. The image generation circuit generates an X-ray image data based on this digital data, and the X-ray image data is output to an image memory. Note that the digital data generated in the X-ray detector 151 by X-ray imaging may be made to be read out by an X-ray detector readout apparatus provided in the X-ray diagnosis apparatus 1 or an X-ray detector readout apparatus other than that of the X-ray diagnosis apparatus 1.

The feature member 153 is extended from the X-ray detector 151. The feature member 153 is imaged by the imager 17. A tip of the feature member 153 is configured by an image recognizable element. The image recognizable element, for instance, is a material such as plastic, metal, and wood, and is desirable to have a color, such as red or yellow, different from that of the bed B or the subject P. Note that the feature member 153 may be detached from the X-ray detector 151 or may be an integral structure with the X-ray detector 151. Likewise, the feature member 153 is an example of an identifier according to the present embodiment.

The imager 17 is located so as to image the X-ray detection unit 15. The imager 17, for instance, images the subject P, the X-ray detector 151, and the feature member 153. The imager 17, for instance, is an optical camera. Likewise, as shown in FIG. 1, The imager 17 according to the present embodiment is located near the X-ray tube 11. Note that, although the imager 17 is located near the X-ray tube 11 in the present embodiment, the position of the imager 17 is arbitrary. For instance, the imager 17 may be located on the support member 19.

The support member 19 is a supporting member that supports the X-ray tube 11 to be movable in a plurality of directions. The support member 19 comprises an arm member 191 and a support body member 193. Note that, although FIG. 1 describes a case where the support member 19 is comprised by the arm member 191 and the support body member 193, the number of support member 19 is arbitrary. For instance, the support member 19 may be comprised by more than three.

The arm member 191, on one end of both ends of the arm member 191, supports the X-ray tube 11 to be movable. Likewise, the other end of both ends of the arm member 191 is supported by the support body member 193. Furthermore, the arm member 191 comprises a first arm 191a, a second arm 191b, and a joint member 191c.

The first arm 191a, on one end of both ends of the first arm 191a, supports the X-ray tube 11 to be slidable and/or rotatable. Likewise, the other end of the first arm 191a is connected to the joint member 191c. The first arm 191a is configured to be extensible and contractible along a longitudinal direction of the first arm 191a, i.e., along a direction of arrow a1 shown in FIG. 1. By the first arm 191a extending and contracting, the X-ray tube 11 slides along the direction of arrow a1. Likewise, the first arm 191a, with the joint member 191c as an axis, is attached to the second arm 191b so as to open or close an angle between the first arm 191a and the second arm 191b. That is to say, the first arm 191a is attached to the second arm 191b via the joint member 191c, openable and closable in a direction of arrow a2 shown in FIG. 1, i.e., a vertical direction.

The second arm 191b is attached to the support body member 193, extensible and contractible in a longitudinal direction of the second arm 191b. That is to say, the second arm 191b is attached to the support body member 193 so as to be vertically movable (slidable) along a direction of arrow a3 shown in FIG. 1. Likewise, as described above, the second arm 191b, via the joint member 191c, supports the first arm 191a to be openable and closable in the direction of arrow a2 shown in FIG. 1.

The joint member 191c, such that the first arm 191a is openable and closable against the second arm 191b in the direction of arrow a2 shown in FIG. 1, connects the first arm 191a and the second arm 191b. A structure of the joint member 191c may be arbitrary, but a stopper mechanism is provided, which, after the operator operates to open or close the angle between the first arm 191a and the second arm 191b, may stop the first arm 191a in an angle which that operation has been ended.

The support body member 193 is a housing that supports the arm member 191. The support body member 193 comprises a body member 193a and a moving member 193b.

The body member 193a has a processing function that controls each member of the X-ray diagnosis apparatus 1, a memory circuit that stores various data, an input interface that receives various operations, and an output interface that outputs various information etc. The body member 193a also executes controls of various processes of imaging the X-ray image.

The moving member 193b is a portable support mechanism provided on a lower portion of the body member 193a, for instance, which is configured by a wheel or a caster etc. The moving member 193b, in response to the operation by the operator, moves in a direction of arrow a4 shown in FIG. 1, i.e., a horizontal direction. Note that the arm member 191 also moves in the direction of arrow a4 shown in FIG. 1 with the movement of the moving member 193b. Likewise, at least one wheel among the wheels provided on the lower portion of the body member 193a may be a driving wheel connected to a driving apparatus such as a motor. In this case, the driving wheel is driven in response to the operation by the operator.

Figure 2:
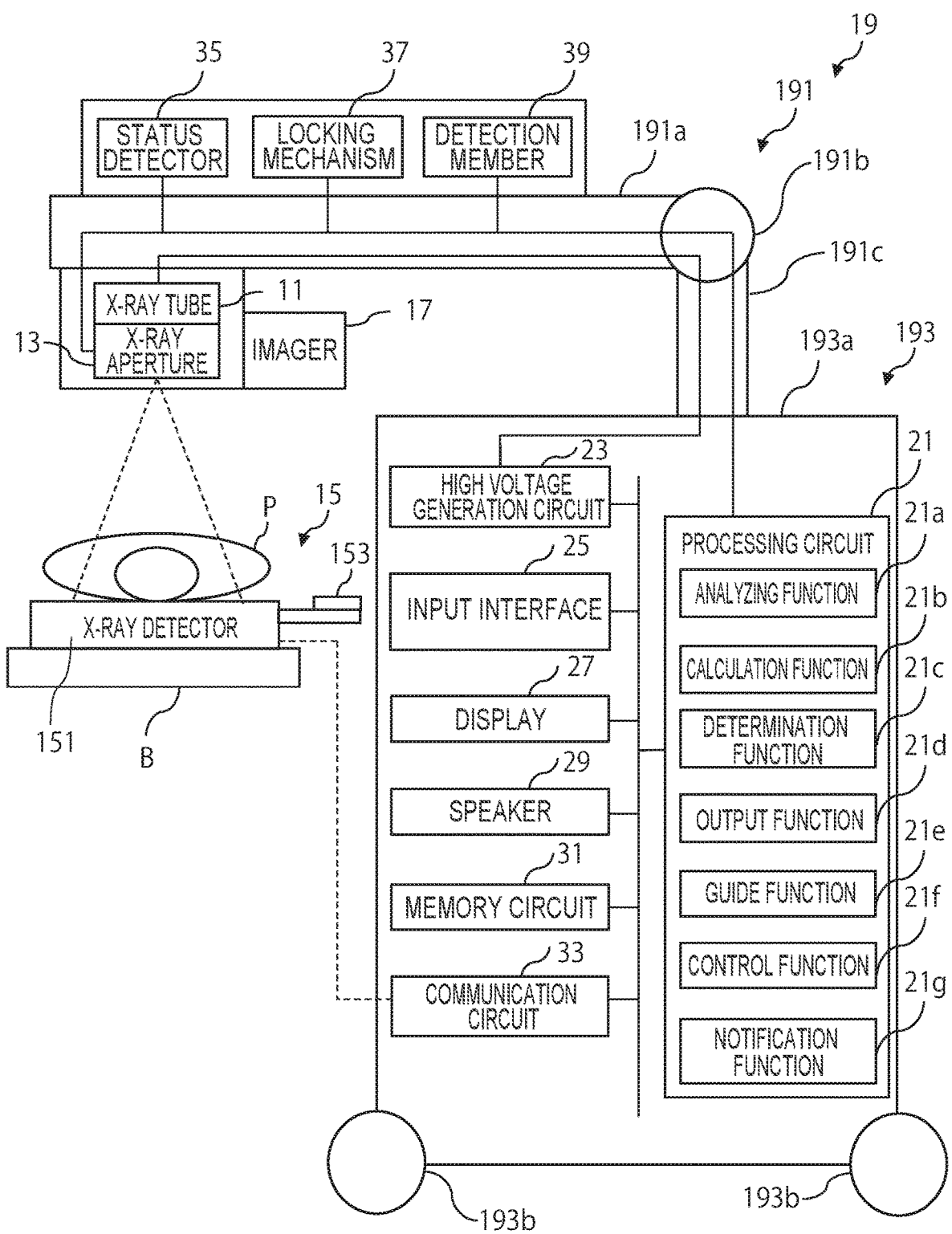
FIG. 2 is a block diagram illustrating a configuration example of the X-ray diagnosis apparatus according to one embodiment.

FIG. 2 is a block diagram illustrating a configuration example of the X-ray diagnosis apparatus 1 according to the present embodiment. As shown in FIG. 2, the X-ray diagnosis apparatus 1 comprises the X-ray tube 11, the X-ray aperture 13, the X-ray detection unit 15, the imager 17, the support member 19, a processing circuit 21, a high voltage generation circuit 23, an input interface 25, a display 27, a speaker 29, a memory circuit 31, a communication circuit 33, a status detector 35, a locking mechanism 37, and a detection member 39.

The processing circuit 21 is a control circuit which performs an entire control of this X-ray diagnosis apparatus 1. Likewise, the processing circuit 21 is an arithmetic circuit which performs various calculations, which, for instance, is configured by processors such as CPU or GPU. The processing circuit 21 according to the present embodiment, for instance, calculates a relative position of the X-ray tube 11 relative to the X-ray detector 151 or calculates an irradiation position of the X-ray tube 11.

For this reason, the processing circuit 21 according to the present embodiment has an analyzing function 21a, a calculation function 21b, a determination function 21c, an output function 21d, a guide function 21e, a control function 21f, and a notification function 21g. The analyzing function 21a is equivalent to an analyzer according to the present embodiment; the calculation function 21b is equivalent to a calculator according to the present embodiment; the determination function 21c is equivalent to the determinator according to the present embodiment, the output function 21d is equivalent to an output according to the present embodiment, the guide function 21e is equivalent to a guider according to the present embodiment, the control function 21f is equivalent to a controller according to the present embodiment, and the notification function 21g is equivalent to a notifier according to the present embodiment.

In the embodiment shown in FIG. 2, each processing function performed in the analyzing function 21a, the calculation function 21b, the determination function 21c, the output function 21d, the guide function 21e, the control function 21f, and the notification function 21g is stored in the memory circuit 31 in the form of computer executable program. The processing function 21 is a processor that realizes functions corresponding to each program by reading out the program from the memory and executing it. In other words, the processing circuit 21 in a state that has read out each program has each function shown in the processing circuit 21 of FIG. 2. Note that, although in FIG. 2, the analyzing function 21a, the calculation function 21b, the determination function 21c, the output function 21d, the guide function 21e, the control function 21f, and the notification function 21g were described to be realized in a single processing circuit 21, these functions may be realized by the processing circuit 21 comprised by combining a plurality of independent processors and each processor executing the programs.

The high voltage generation circuit 23 has various control circuits to control the tube current, the tube voltage, and an imaging time etc., a high voltage converter, a high voltage rectifier, and a filament transformer etc. Specifically, the high voltage generation circuit 23, under the control of the processing circuit, following an X-ray imaging condition, supplies the tube current suitable for X-ray imaging to the X-ray tube 11 and applies the tube voltage suitable for X-ray imaging to the X-ray tube 11. Here, the X-ray imaging condition, for instance, is condition about X-ray imaging such as the tube current or tube voltage, irradiating time, source image distance (hereinafter referred to as SID), a size of an X-ray field, imaging portion, imaging type, or configuration of the X-ray tube 11.

The input interface 25, for instance, receives various input operation from the operator, converts the received input operation into electrical signal, and outputs to the processing circuit 21. For instance, the input interface 25 receives an input of information about the subject P or the X-ray imaging condition while imaging the subject P, etc. The input interface 25, for instance, is realized by a mouse or a keyboard, a trackball, a manual switch, a foot switch, a button, a joystick, etc. Note that the input interface 25 may be configured by a tablet terminal able to wirelessly communicate with a body of the X-ray diagnosis apparatus 1.

The display 27 is connected to the processing circuit 21 etc., and displays various image or information based on a signal supplied from the processing circuit 21 etc. For instance, the display 27 displays an image imaged by the imager 17, a movement route that will be explained later, or a Graphical User Interface (GUI) to receive various operations from the operator, etc. In the present embodiment, the display 27, for instance, is configured by a liquid crystal display or a Cathode Ray Tube (CRT) display, etc.

The speaker 29 is connected to the processing circuit 21 etc., and outputs various information by sound based on the signal supplied from the processing circuit 21 etc. For instance, the speaker 29 outputs the movement route that will be described later by sound. Note that the speaker 29 may be built-in in the display 27.

The memory circuit 31, for instance, may be realized by a semiconductor memory element such as a Random Access Memory (RAM) or a flash memory, a hard disk, or an optical disc, etc. In the present embodiment, for instance, the memory element 31 stores program executed in circuits included in the X-ray diagnosis apparatus 1 or results calculated by the calculation function 21b, etc.

The communication circuit 33 is a transmitter/receiver circuit with an antenna for wireless communication with the X-ray detector 151. The communication circuit 33, for instance, after receiving X-ray image data from the X-ray detector 151, stores this X-ray image data in the memory circuit 31.

The status detector 35 detects a movement amount of each of a plurality of movable directions of the X-ray tube 11 and outputs it to the memory circuit 21. The status detector 35, for instance, is mounted on the support member 19. The status detector 35 is configured by a potentiometer detecting the movement amount, an encoder which is a position detecting sensor, etc. The encoder, for instance, is a so-called absolute encoder such as that of a magnetic, a brush, or a photoelectric method. Likewise, various types of detectors such as a rotary encoder that outputs rotational displacement into digital signal or a linear encoder that outputs linear displacement into digital signal may be appropriately used as the status encoder 35.

Note that, in the example shown in FIG. 2, although the status detector 35 is provided on the first arm 191a, a place to provide the status detector 35 is not limited to this. The status detector 35 may be provided on the second arm 191b, the joint member 191c, or the support body member 193. Furthermore, the status detector 35 is not limited to be mounted on one place but may be provided on a plurality of places. That is to say, a number of the status detector 35 is arbitrary, and it is sufficient when the status detector 35 is provided on at least one place of the support member 19.

The locking mechanism 37 is a mechanism to lock the movement of the X-ray tube 11. The locking mechanism 37 performs a locking operation under the control of the processing circuit 21. Specifically, the locking mechanism 37 is a mechanism to lock the extension and contraction of the first arm 191a, the rotation of the first arm 191a, the vertical movement of the second arm 191b, or the movement of the moving member 193b, which, for instance, is realized by a lock pin, an electronic lock, or a brake etc.

Note that, in the example shown in FIG. 2, although the locking mechanism 37 is provided on the first arm 191a, the place to provide the locking mechanism 37 is not limited to this. The locking mechanism 37 may be provided on the second arm 191b, the joint member 191c, or the support body member 193. Furthermore, the locking mechanism 37 is not limited to be mounted on one place but may be provided on the plurality of places. That is to say, a number of locking mechanism 37 is arbitrary, and it is sufficient when the locking mechanism 37 is provided on at least one place of the support member 19.

The detection member 39 detects the movement of the X-ray tube 11 and outputs it to the processing circuit 21. The detection member, for instance, is realized by an accelerometer or a gyro-sensor etc. Note that, in the example shown in FIG. 2, although the detection member 39 is provided on the first arm 191a, the place to provide the detection member 39 is not limited to this. The detection member 39 may be provided on the second arm 191b, the joint member 191c, or the support body member 193. Furthermore, the detection member 39 is not limited to be mounted on one place but may be provided on the plurality of places. That is to say, a number of the detection member 39 is not limited to one place, and it is sufficient when the detection member 39 is provided on at least one place of the support member 19.

In the present embodiment, the status detector 35 may be made to detect the movement of the X-ray tube 11 instead of the detection member 39. That is to say, when the status detector 35 detects the movement of the X-ray tube 11, the detection member 39 may be omitted. In the present embodiment, when the detection member 39 is omitted, the status detector 35 is equivalent to the detection member according to the present embodiment.

Figure 3:
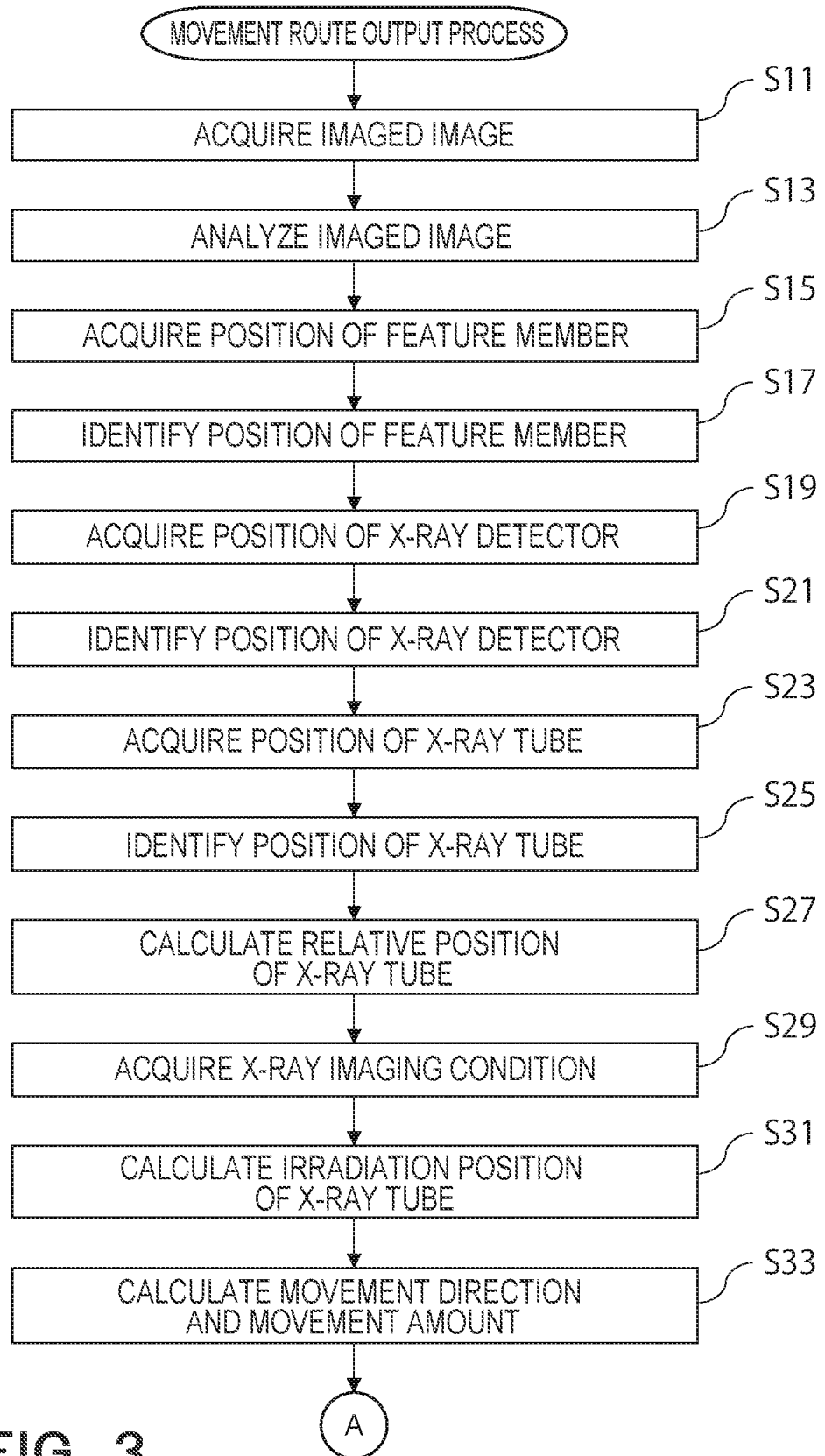
FIG. 3 is a flowchart explaining a content of a movement route output process executed in the X-ray diagnosis apparatus according to one embodiment.
Figure 4:
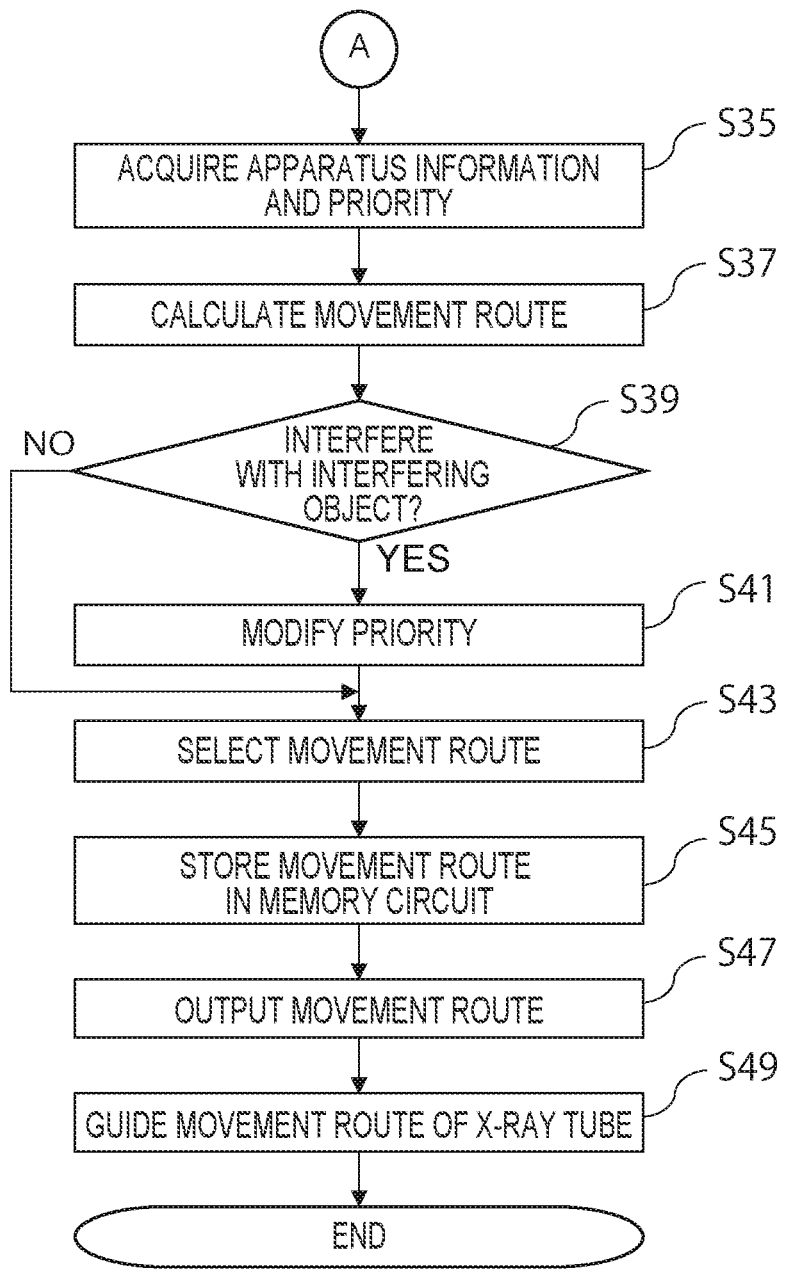
FIG. 4 is a flowchart explaining a content of the movement route output process executed in the X-ray diagnosis apparatus according to one embodiment.

FIGS. 3 and 4 are flowcharts explaining a content of a movement route output process executed in the X-ray diagnosis apparatus 1 according to the present embodiment. In this movement route output process, a relative position of the X-ray tube 11 relative to the X-ray detector 151 and an irradiation position of the X-ray tube 11 which meets the X-ray imaging condition for which this relative position is predetermined are calculated, or based on the relative position of the X-ray tube 11 relative to the X-ray detector 151 and the irradiation position of the X-ray tube 11, the movement route of the X-ray tube 11 is output. For instance, this movement route output process is a process executed when the operator inputs the X-ray imaging condition via the input interface 25.

As shown in FIG. 3, first, the X-ray diagnosis apparatus 1 acquires an image which images the feature member 153 that identifies the position of the X-ray detector 151 (imaged image) (Step S11). The process of acquiring the image that images this feature member 153 is realized by the analyzing function 21a in the processing circuit 21. Specifically, the X-ray diagnosis apparatus 1, by the imager 17, acquires the image which images the feature member 153 that identifies the position of the X-ray detector 151.

Figure 5:
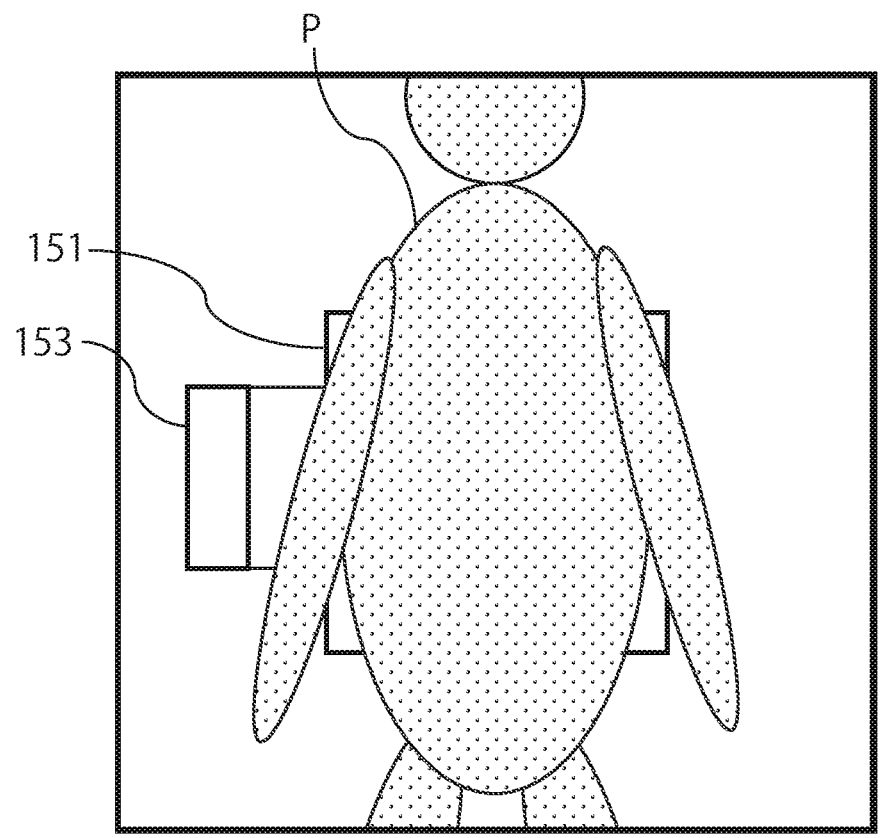
FIG. 5 is a diagram illustrating an example of a feature member imaged by the imager in the X-ray diagnosis apparatus according to one embodiment.

FIG. 5 is a diagram illustrating an example of the image which images the feature member 153 that identifies the position of the X-ray detector 151, in the X-ray diagnosis apparatus 1 according to the present embodiment. As shown in FIG. 5, in the present embodiment, in the image which images the feature member 153 that identifies the position of the X-ray detector 151, the subject P, the X-ray detector 151, and the feature member 153 are imaged. Note that, the image which images the feature member 153 that identifies the position of the X-ray detector 151, may be an image which the subject P and the feature member 153 are imaged. Likewise, the image which images the feature member 153 that identifies the position of the X-ray detector 151 may be an image continuously imaged like a moving image or an image imaged like a still image.

Next, as shown in FIG. 3, the X-ray diagnosis apparatus 1 analyzes the image which images the feature member 153 that identifies the position of the X-ray detector 151 (Step S13). The process of analyzing the image which the feature member 153 is imaged is realized by the analyzing function 21a in the processing circuit 21. Specifically, the X-ray diagnosis apparatus 1, at Step S11, analyzes the image which images the feature member 153 that identifies the position of the X-ray detector 151. More specifically, first, the analyzing function 21a, by image analyzing the image which images the feature member 153 that identifies the position of the X-ray detector 151, identifies the feature member 153 in the image. Next, the analyzing function 21a, by image analyzing the image which images the feature member 153 that identifies the position of the X-ray detector 151, acquires a size of feature member 153 in the image.

Next, as shown in FIG. 3, the X-ray diagnosis apparatus 1 acquires a position of the feature member 153 (Step S15). The process of acquiring the position of the feature member 153 is realized by the calculation function 21b in the processing circuit 21. Specifically, the X-ray diagnosis apparatus 1, using a formula that represents a relationship between the size of feature member 153 and the distance from the feature member 153 to the imager 17, calculates the distance from the feature member 153 to the imager 17 based on the size of the feature member 153 acquired at Step S13, and acquires the position of the feature member 153. The formula representing the relationship between the size of the feature member 153 and the distance from the feature member 153 to the imager 17 is stored in advance in the memory circuit 31. The position of the feature member 153, for instance, is a center of the feature member 153.

Note that, although the distance from the feature member 153 to the imager 17 was calculated using the formula representing the relationship between the size of feature member 153 and the distance from the feature member 153 to the imager 17, a method of calculating the distance from the feature member 153 to the imager 17 is not limited to this. For instance, a correspondence table between the size of the feature member 153 and the distance from the feature member 153 to the imager 17 may be stored in advance in the memory circuit 31, and based on this correspondence table, the distance from the feature member 153 to the imager 17 may be calculated.

Likewise, the distance from the feature member 153 to the imager 17, by imaging the feature member 153 from two or more different positions with moving image imaging etc., may be made to be calculated based on the imaged image. Furthermore, the distance from the feature member 153 to the imager 17, by using a stereo camera as the imager 17, may be made to be measured based on a parallax value according to the stereo camera.

Likewise, the position of the feature member 153 was the center of the feature member 153, but is not limited to this. The position of the feature member 153 is arbitrary. The position of the feature member 153, for instance, may be four corners of the feature member 153.

Next, as shown in FIG. 3, the X-ray diagnosis apparatus 1 identifies the position of the feature member 153 (Step S17). The process of identifying the position of the feature member 153 is realized by the calculation function 21b in the processing circuit 21. Specifically, the X-ray diagnosis apparatus 1, based on the distance from the feature member 153 to the imager 17 acquired at Step S15, identifies the position of the feature member 153 with its origin at the position of the imager 17.

Next, as shown in FIG. 3, the X-ray diagnosis apparatus 1 acquires the position of the X-ray detector 151 (Step S19). The process of acquiring the position of the X-ray detector 151 is realized by the calculation function 21b in the processing circuit 21. Specifically, the X-ray diagnosis apparatus 1 acquires the distance from the position of the feature member 153 to the position of the X-ray detector 151 stored in advance in the memory circuit 31, and acquires the position of the X-ray detector 151 relative to the position of the feature member 153.

Figure 6:
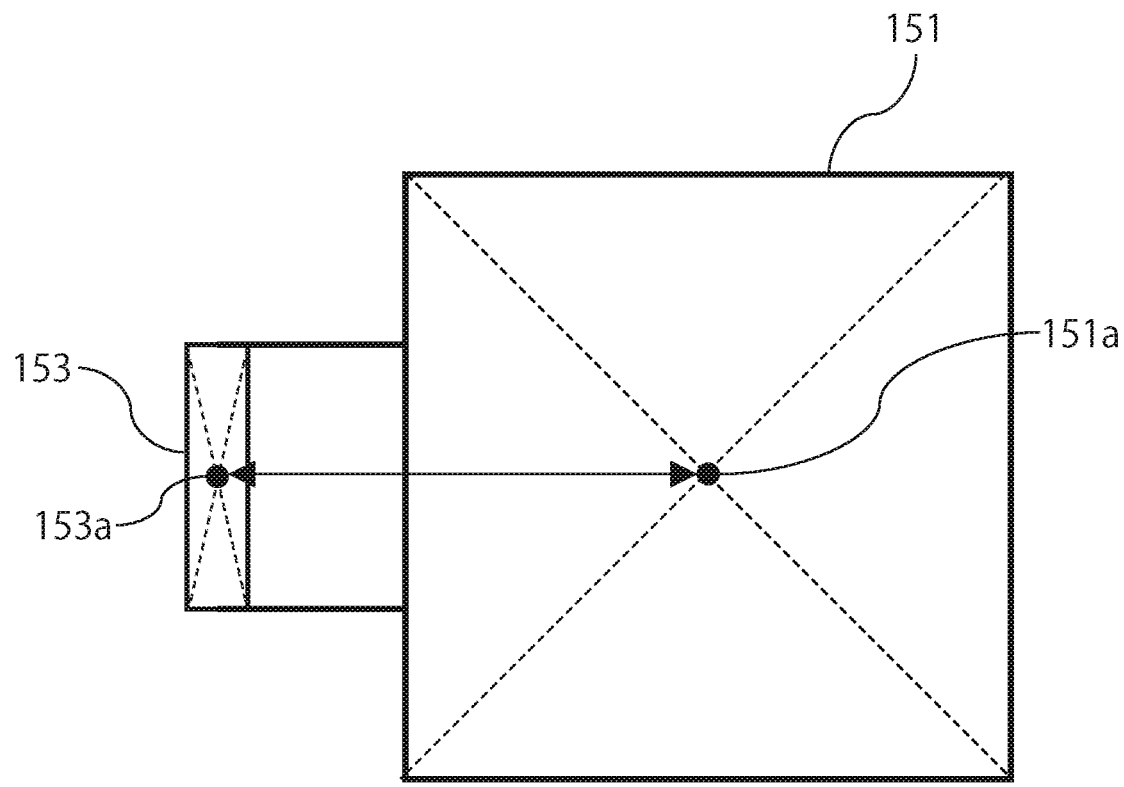
FIG. 6 is a diagram illustrating an example of a positional relationship between a position of the feature member and a position of an X-ray detector in the X-ray diagnosis apparatus according to one embodiment.

FIG. 6 is a diagram illustrating an example of a positional relationship between the position 153a of the feature member 153 and the position 151a of the X-ray detector 151 in the X-ray diagnosis apparatus according to the present embodiment. As shown in FIG. 6, for instance, the position 151a of the X-ray detector 151 is the center of the X-ray detector 151. For this reason, the distance from the position 153a of the feature member 153 to the position 151a of the X-ray detector 151 is, as shown with an arrow of FIG. 6, the distance between center points of the X-ray detector 151 and the feature member 153. That is to say, the X-ray diagnosis apparatus 1, at Step S19, based on the distance between the center points of the X-ray detector 151 and the feature member 153, acquires the position 151a of the X-ray detector 151 relative to the position 153a of the feature member 153. Note that, the position 151a of the X-ray detector 151 was the center of the X-ray detector 151, but is not limited to this. The position 151a of the X-ray detector 151 is arbitrary, for instance, may be four corners of the X-ray detector 151.

Likewise, the distance from the position 153a of the feature member 153 to the position 151a of the X-ray detector 151 may be made to set a different value in response to a type of the X-ray detector 151 and store it in the memory circuit 31. When setting a different value in response to the type of the X-ray detector 151, for instance, different values are associated in response to the type of the X-ray detector 151 for every color or shape of the feature member 153. That is to say, the X-ray diagnosis apparatus 1 stores an associated list that associates the color or shape of the feature member 153 with the distance from the position 153a of the feature member 153 to the position 151a of the X-ray detector 151 in the memory circuit 31. Then, by image analyzing the image which the feature member 153 that identifies the position 151a of the X-ray detector 151 is imaged, the color or shape of the feature member 153 may be identified, and based on the identified color or shape of the feature member 153, the distance from the position 153a of the feature member 153 to the position 151a of the X-ray detector 151 may be made to be acquired from the associated list.

Next, as shown in FIG. 3, the X-ray diagnosis apparatus 1 identifies the position 151a of the X-ray detector 151 (Step S21). The process of identifying the position 151a of the X-ray detector 151 is realized by the calculation function 21b in the processing circuit 21. Specifically, the X-ray diagnosis apparatus 1, based on the position 153a of the feature member 153 with its origin at the position of the imager 17 identified at Step S17, and the position 151a of the X-ray detector 151 relative to the position 153a of the feature member 153 acquired at Step S19, identifies the position 151a of the X-ray detector 151 with its origin at the position of the imager 17.

Next, as shown in FIG. 3, the X-ray diagnosis apparatus 1 acquires the position of the X-ray tube 11 (Step S23). The process of acquiring the position of the X-ray tube 11 is realized by the calculation function 21b in the processing circuit 21. Specifically, the X-ray diagnosis apparatus 1 acquires the distance from the position of the X-ray tube 11 to the position of the imager 17 stored in advance in the memory circuit 3. Here, the position of the X-ray tube 11, for instance, is the tube focus position 11a which is a position of tube focus of the X-ray tube 11.

Next, as shown in FIG. 3, the X-ray diagnosis apparatus 1 identifies the position of the X-ray tube 11 (Step S25). The process of identifying the position of the X-ray tube 11 is realized by the calculation function 21b in the processing circuit 21. Specifically, the X-ray diagnosis apparatus 1, based on the distance from the X-ray tube 11 to the position of the imager 17 acquired at Step S23, identifies the position of the X-ray tube 11 with its origin at the position of the imager 17.

Next, as shown in FIG. 3, the X-ray diagnosis apparatus 1 calculates the relative position of the X-ray tube 11 relative to the X-ray detector 151 (Step S27). The process of calculating the relative position of the X-ray tube 11 is realized by the calculation function 21b in the processing circuit 21. Specifically, the X-ray diagnosis apparatus 1, based on the position 151a of the X-ray detector 151 with its origin at the position of the imager 17 identified at Step S21 and the position of the X-ray tube 11 with its origin at the position of the imager 17 identified at Step S25, calculates the relative position of the X-ray tube 11 relative to the X-ray detector 151 with its origin at the position of the imager 17. The relative position of the X-ray tube 11 relative to the X-ray detector 151 is a current position of the X-ray tube 11 relative to the X-ray detector 151 with its origin at the position of the imager 17.

Next, as shown in FIG. 3, the X-ray diagnosis apparatus 1 acquires the X-ray imaging condition (Step S29). The process of acquiring the X-ray imaging condition is realized by the calculation function 21b in the processing circuit 21. Specifically, the X-ray diagnosis apparatus 1, from information input by the operator via the input interface 25 and/or the memory circuit 31, acquires SID or information about a configuration of X-ray tube 11 as the X-ray imaging condition. The information about the configuration of the X-ray tube 11 is information about the configuration of the X-ray tube 11 relative to the detection surface of the X-ray detector 151, which includes information such as configuring the X-ray tube 11 to face against the detection surface of the X-ray detector 151 or configuring the X-ray tube 11 to be tilted by a predetermined angle.

Next, as shown in FIG. 3, the X-ray diagnosis apparatus 1 calculates the irradiation position of the X-ray tube 11 that meets the X-ray imaging condition for which the relative position of the X-ray tube is predetermined (Step S31). The process of calculating the irradiation position of the X-ray tube 11 is realized by the calculation function 21b in the processing circuit 21. Specifically, the X-ray diagnosis apparatus 1, based on the position 151a of the X-ray detector 151 with its origin at the position of the imager 17 identified at Step S21 and the X-ray imaging condition acquired at Step S29, calculates the irradiation position of the X-ray tube 11 with its origin at the position of the imager 17. The irradiation position of the X-ray tube 11 is a position aligning to the X-ray detector 151 and a position meeting the SID, which is a target position of the X-ray tube 11.

Figure 7:
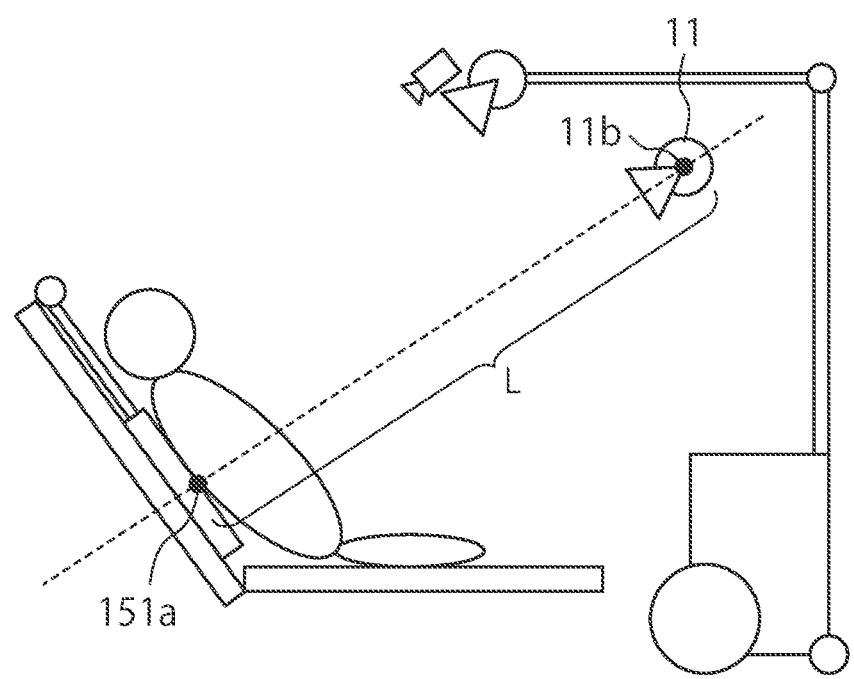
FIG. 7 is a diagram illustrating an example of an irradiation position of an X-ray tube in the X-ray diagnosis apparatus according to one embodiment.

FIG. 7 is a diagram illustrating an example of the irradiation position 11b of the X-ray tube 11 in the X-ray diagnosis apparatus 1 according to the present embodiment. In the example shown in FIG. 7, the X-ray imaging condition acquired at Step S29 is a condition where the SID is distance L from the position 151a of the X-ray detector 151, configuring the X-ray tube 11 to face against the detection surface of the X-ray detector 151. Therefore, the irradiation position 11b of the X-ray tube 11, as shown in FIG. 7, is on the normal line of the detection surface of the X-ray detector 151 passing through the position 151a of the X-ray detector 151, and is a position in distance L from the position 151a of the X-ray detector 151. Note that, in the example shown in FIG. 7, the configuration of the X-ray tube 11 faces against the detection surface of the X-ray detector 151, but is not limited to this. The configuration of the X-ray tube 11 relative to the detection surface of the X-ray detector 151 is arbitrary. For instance, the X-ray tube 11 may be configured to be tilted by a predetermined angle relative to the detection surface of the X-ray detector 151.

Next, as shown in FIG. 3, the X-ray diagnosis apparatus 1 calculates a movement direction and the movement amount of the X-ray tube 11 from the relative position of the X-ray tube 11 relative to the X-ray detector 151 to the irradiation position 11b of the X-ray tube 11 (Step S33). The process of calculating a movement information of the X-ray tube 11 is realized by the calculation function 21b in the processing circuit 21. Specifically, the X-ray diagnosis apparatus 1, based on the relative position of the X-ray tube 11 relative to the X-ray detector 151 calculated at Step S27 and the irradiation position 11b of the X-ray tube 11 calculated at Step 31, calculates the movement direction and the movement amount of the X-ray tube 11 from the relative position of the X-ray tube 11 relative to the X-ray detector 151 to the irradiation position 11b of the X-ray tube 11.

Figure 8:
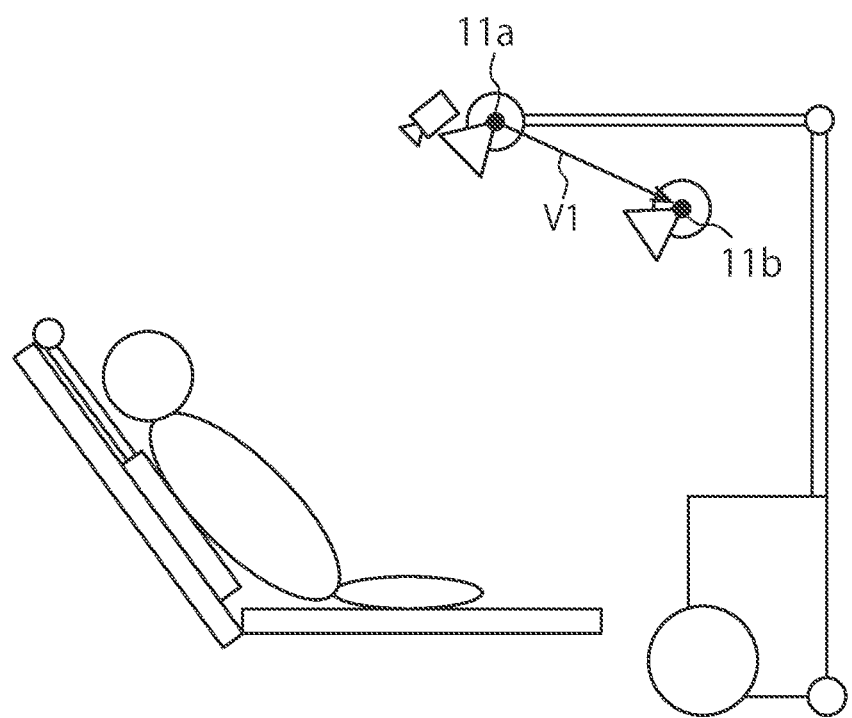
FIG. 8 is a diagram illustrating an example of a movement direction and a movement amount from a relative position of the X-ray tube to the irradiation position of the X-ray tube in the X-ray diagnosis apparatus according to one embodiment.

FIG. 8 is a diagram illustrating an example of the movement direction and the movement amount from the relative position of the X-ray tube 11 relative to the X-ray detector 151 to the irradiation position 11b of the X-ray tube 11 in the X-ray diagnosis apparatus 1 according to the present embodiment. In the example shown in FIG. 8, the calculation function 21b calculates a vector V1 from the relative position of the X-ray tube 11 relative to the X-ray detector 151 to the irradiation position 11b of the X-ray tube 11. Vector V1 indicates the movement direction and the movement amount from the relative position of the X-ray tube 11 relative to the X-ray detector 151 to the irradiation position 11b of the X-ray tube 11.

Next, as shown in FIG. 4, the X-ray diagnosis apparatus 1 acquires an apparatus information about the X-ray diagnosis apparatus 1 and a priority associated with the apparatus information (Step S35). The process of acquiring the apparatus information and the priority is realized by the calculation function 21b in the processing circuit 21. Specifically, the X-ray diagnosis apparatus 1 acquires the apparatus information about the X-ray diagnosis apparatus 1 and the priority associated with the apparatus information from the memory circuit 31.

Here, the apparatus information about the X-ray diagnosis apparatus 1 is information about the plurality of movable directions of the X-ray tube 11. The information about the plurality of movable directions of the X-ray tube 11, for instance, includes information that the first arm 191a is extensible and contractible in direction a1, information that the first arm is rotatable in direction a2 against the second arm 191b, information that the second arm 191b is vertically movable in direction a3, or information that the body member 192a is movable by the moving member 192b in direction a4, etc. Likewise, the priority is associated with the information about the plurality of movable directions of the X-ray tube 11. This priority is used when selecting the movement route of the X-ray tube 11 at Step S43, which will be described later. Likewise, the priority may be preset to the information about the plurality of movable directions of the X-ray tube 11 by the operator. Note that the priority may be modified by the operator via the input interface 25.

Next, as shown in FIG. 4, the X-ray diagnosis apparatus 1 calculates the movement route for the X-ray tube 11 to move from the relative positions of the X-ray tube 11 relative to the X-ray detector 151 to the irradiation position 11b of the X-ray tube 11 (Step S37). The process of calculating the movement route is realized by the calculation function 21b in the processing circuit 21. Specifically, based on the movement direction and movement amount of the X-ray tube 11 from the relative positions of the X-ray tube 11 relative to the X-ray detector 151 calculated at Step S33 to the irradiation positions 11b of the X-ray tube 11, and the apparatus information about the X-ray diagnosis apparatus 1 and the priority associated with the apparatus information acquired at Step S35, the X-ray diagnosis apparatus 1 calculates a plurality of movement routes for the X-ray tube 11 to move from the relative positions of the X-ray tube 11 relative to the X-ray detector 151 to the irradiation positions 11b of the X-ray tube 11. Here, the movement route is an information that represents the movement direction and movement amount of the X-ray tube 11 from the relative positions of the X-ray tube 11 relative to the X-ray detector 151 to the irradiation positions 11b of the X-ray tube 11, and the movement route calculated by the calculation function 21b is an example of the movement information according to the present embodiment. Note that, at step 37, the plurality of movement routes were calculated, but the number of movement routes to be calculated is arbitrary. For instance, only one movement route may be calculated.

Figure 9:
FIG. 9 is a diagram illustrating an example of a movement route list of a movement route calculated in a calculation function in the X-ray diagnosis apparatus according to one embodiment.

FIG. 9 is a diagram illustrating an example of a movement route list LT1 of the movement route calculated by the calculation function 21b in the X-ray diagnosis apparatus 1 according to the present embodiment. In the example shown in FIG. 9, the plurality of movable directions of the X-ray tube 11 is arm extension and contraction, arm's vertical movement, arm rotation, and body movement; the priority is configured with 1~4 associated in order with the arm extension and contraction, arm's vertical movement, arm rotation, and body movement. With a route 1 shown in FIG. 9 as an example, the route 1 indicates that "movable direction: arm extension and contraction, movement amount: −5" and "movable direction: arm's vertical movement, movement amount: −2." That is to say, in the example of route 1 shown in FIG. 9, the operator may move the X-ray tube 11 from the relative positions of the X-ray tube 11 relative to the X-ray detector 151 to the irradiation positions 11*b* of the X-ray tube 11 by moving the first arm 191*a* by 5 in a contracting direction and moving the second arm 191*b* by 2 in a downward direction. Note that, in FIG. 9, the movement amount of each of the plurality of movable directions of the support member 19 indicates a case where the first arm 191*a* moves in the contracting direction, a case where the second arm 191*b* moves downward, a case where the first arm 191*a* rotates counterclockwise, and a case where the body member 192 moves away from the subject P, as negative directions.

Next, as shown in FIG. 4, the X-ray diagnosis apparatus 1 determines whether the X-ray tube 11 and/or the support member 19 interferes with an interfering object which includes subject P (Step S39). The process of determining whether it interferes with the interfering object is realized by the determination function 21*c* in the processing circuit 21. Specifically, the X-ray diagnosis apparatus 1 performs image analyzing to the image imaged by the imager 17 acquired at Step S11, and based on the result of the image analysis and the movement route calculated at Step S37, by the movement of the X-ray tube 11, when it determines that the X-ray tube 11 and/or the support member 19 interferes with the interfering object which includes subject P (Step S39: Yes), the X-ray diagnosis apparatus 1 modifies a preset priority (Step S41). More specifically, in the example shown in FIG. 9, the X-ray diagnosis apparatus 1, for instance, by moving the first arm 191*a* by 5 in the contracting direction at route 1, when determining that the X-ray tube 11 and/or the first arm 191*a* interferes with the interfering object, sets the priority associated with the arm extension and contraction as 4, and modifies the priority by moving up each priority associated with other plurality of movable directions by 1.

After the process of Step S41, or at Step S39 described above, performing image analysis on the image imaged by the imager 17 acquired at Step S11, and based on the result of the image analysis and the movement route calculated at Step S37, by the movement of the X-ray tube 11, when it determines that the X-ray tube 11/and the support member 19 and the interfering object including the subject P does not interfere (Step S39: No), the X-ray diagnosis apparatus 1 selects the movement route (Step S43). The process of selecting the movement route is realized by the calculating function 21*b* in the processing circuit 21.

Specifically, the X-ray diagnosis apparatus 1, based on the movement route list LT1, for each movement route, calculates a sum of the priority associated with each of the plurality of movable directions of the X-ray tube 11 for which the movement amount is calculated. Then, the X-ray diagnosis apparatus 1 selects the movement route for which the calculated sum of priority has the lowest value. In the example shown in FIG. 9, since the movement amount of the arm extension and contraction and the movement amount of the arm's vertical movement is calculated for route 1, the sum of priority in route 1 is 3, which is the sum of priority associated with the arm extension and contraction and the arm's vertical movement. Likewise, since the movement amount of the arm's vertical movement and the movement amount of the body movement is calculated for route, 2, the sum of priority in route 2 is 6, which is the sum of priority associated with the arm's vertical movement and the body movement. Likewise, since the movement amount of arm extension and contraction and the movement amount of arm rotation is calculated for route 3, it becomes 4 which is the sum of priority associated with the arm extension and contraction and the arm rotation. Therefore, in the example shown in FIG. 9, the X-ray diagnosis apparatus 1 calculates the sum of priority associated with each of the plurality of movable directions of the X-ray tube 11 for which the movement amount is calculated, and route 1 which has the lowest value is selected as the movement route.

Note that the X-ray diagnosis apparatus 1 calculates the sum of priority associated with each of the plurality of movable directions of the X-ray tube 11 for which the movement amount is calculated and selects the movement route which has the lowest value, but the method of selecting the movement route is not limited to this. For instance, the X-ray diagnosis apparatus 1 may calculate a product of priority associated with each of the plurality of movable directions of the X-ray tube 11 for which the movement amount is calculated and select the movement route which has the lowest value, or may select the movement route by other methods. Likewise, if only one movement route is calculated at Step 33, Step S39 through Step S43 may be omitted.

Next, as shown in FIG. 4, the X-ray diagnosis apparatus 1 stores the movement route in the memory circuit 31 (Step S45). The process of storing the movement route in the memory circuit 31 is realized by the calculation function 21*b* in the processing circuit 21. Specifically, the X-ray diagnosis apparatus 1 stores the movement route selected at Step S43 in the memory circuit 31.

Next, as shown in FIG. 4, the X-ray diagnosis apparatus 1 outputs the movement route (Step S47). The process of outputting the movement route is realized by the output function 21*d* in the processing circuit 21. Specifically, the X-ray diagnosis apparatus 1 outputs the movement route selected at Step S43 to the display 27, the speaker 29, or a printed circuit.

Next, as shown in FIG. 4, the X-ray diagnosis apparatus 1 guides the movement of the X-ray tube 11 (Step S49). The process of guiding the X-ray tube 11 is realized by the guide function 21*e* in the processing circuit 21. Specifically, based on the movement route output at Step S47, the X-ray diagnosis apparatus 1 guides the movement of the X-ray tube 11 to the operator. More specifically, when the movement route is output to the display 21, the X-ray diagnosis apparatus 1 guides the movement of the X-ray tube 11 to the operator via the display 27. Likewise, when the movement route is output to the speaker 29, the X-ray diagnosis apparatus 1 guides the movement of the X-ray tube 11 to the operator by voice via the speaker 29. Note that the movement of the X-ray tube 11 may be guided via the printed circuit.

By executing Step S49, the movement route output process according to the present embodiment ends.

Figure 10:
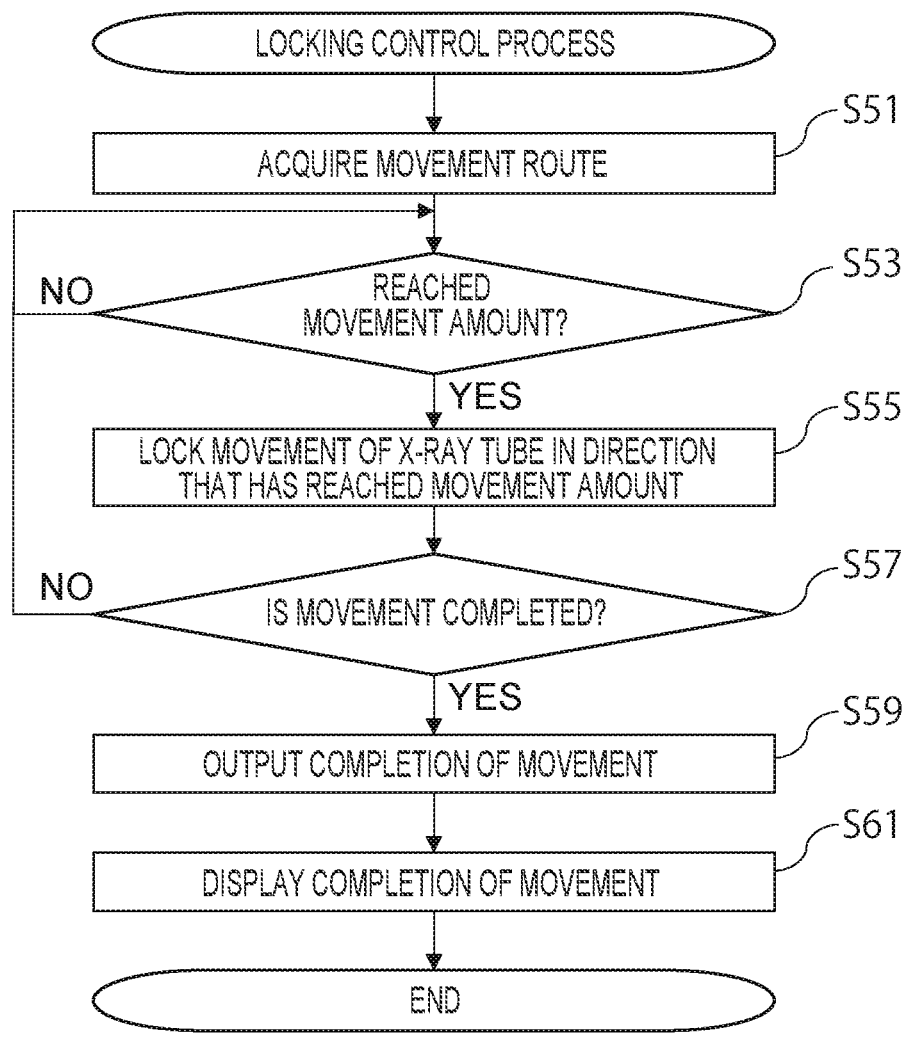
FIG. 10 is a flowchart explaining a content of a locking control process executed in the X-ray diagnosis apparatus according to one embodiment.

Next, a locking control process, executed by the X-ray diagnosis apparatus 1 according to the present embodiment, that controls the locking mechanism 37 of the support member 19 to lock the movement of the X-ray tube 11 in directions for which it has reached the movement amount calculated by the calculation function 21*b* will be described. FIG. 10 is a flowchart explaining a content of the locking control process executed by the X-ray diagnosis apparatus 1 according to the present embodiment. For instance, the locking control process is a process executed when the X-ray diagnosis apparatus 1 acquires the movement route from the memory circuit 31 and the operator starts the movement of the X-ray tube 11.

As shown in FIG. 10, first, the X-ray diagnosis apparatus 1 acquires the movement route (Step S51). The process of acquiring the movement route is realized by the control function 21*f* in the processing circuit 21. Specifically, the X-ray diagnosis apparatus 1 acquires the movement route stored in the memory circuit 31.

Next, as shown in FIG. 10, the X-ray diagnosis apparatus 1 determines whether the movement of the X-ray tube 11 has reached the movement amount of each of the plurality of movable directions of the X-ray tube 11 (Step S53). The process of determining whether the movement has reached this movement amount is realized by the control function 21*f* in the processing circuit 21. Specifically, based on the movement amount of each of the plurality of movable directions of the X-ray tube 11 detected by the status detector 35 and the movement route acquired at Step S51, when the movement of the X-ray tube 11 has not reached the movement amount of the movement route acquired at Step S51 (Step S53: No), the X-ray diagnosis apparatus 1 standbys, repeating the process of Step S53 until the movement of the X-ray tube 11 reaches the movement amount of the movement route acquired at Step S51.

On the other hand, at Step S53, based on the movement amount of each of the plurality of movable directions of the X-ray tube 11 detected by the status detector 35 and the movement route acquired at Step S51, when the movement of the X-ray tube 11 has reached the movement amount of the movement route acquired at Step S51 (Step S53: Yes), the X-ray diagnosis apparatus 1 locks the movement of the X-ray tube 11 in the direction which has reached the movement amount (Step S55). The process of locking the movement of the X-ray tube 11 in the direction which has reached the movement amount is realized by the control function 21*f* in the processing circuit 21. Specifically, the X-ray diagnosis apparatus 1, based on the movement amount of each of the plurality of movable directions of the X-ray tube 11 detected by the status detector 35 and the movement route acquired at Step S51, by the control function 21*f*, controls the locking mechanism 37 of the support member 19 that supports the X-ray tube 11 to be movable in the direction which has reached the movement amount and locks the movement of the X-ray tube 11 in the direction which has reached the movement amount.

Note that the X-ray diagnosis apparatus 1, at Step S53, acquires the movement amount of each of the plurality of movable directions of the X-ray tube 11 by using the status detector 35, but the method of acquiring the movement amount of each of the plurality of movable directions of the X-ray tube 11 is not limited to this. The movement amount of each of the plurality of movable directions of the X-ray tube 11 may be acquired by other methods. That is to say, the method of acquiring the movement amount of each of the plurality of movable directions of the X-ray tube 11 is arbitrary.

For instance, the X-ray diagnosis apparatus 1, based on the images imaged by the imager 17 before or after the movement of the X-ray tube 11, may calculate and acquire the movement amount of each of the plurality of movable directions of the X-ray tube 11. That is to say, the X-ray diagnosis apparatus 1, based on the feature member 153 shown on the image imaged before the movement of the X-ray tube 11, calculates the relative positions of the X-ray tube 11 relative to the feature member 153 before its movement. Then, after the movement of the X-ray tube 11, the X-ray diagnosis apparatus 1, based on the feature member 153 shown on the image imaged after the movement of the X-ray tube 11, may calculate the relative positions of the X-ray tube 11 relative to the feature member 153 after its movement, and based on a difference of the relative positions of the X-ray tube 11 relative to the feature member 153 before and after its movement, may acquire the movement amount of each of the plurality of movable directions of the X-ray tube 11.

Note that the X-ray diagnosis apparatus 1 calculates and acquires the movement amount of each of the plurality of movable directions of the X-ray tube 11 based on the difference of the relative positions of the X-ray tube 11 relative to the feature member 153 before and after its movement, but is not limited to this and may be made to calculate and acquire the movement amount of each of the plurality of movable directions of the X-ray tube 11 based on other differences. That is to say, the difference used to calculate and acquire the movement amount of each of the plurality of movable directions of the X-ray tube 11 is arbitrary, which, for instance, may be based on a difference of the relative positions of the X-ray tube 11 relative to the X-ray detector 151 before and after its movement or relative to other feature points, based on a difference of the relative positions of the imager 17 relative to the feature member 153 before and after its movement, or based on the relative positions of the X-ray tube 11 relative to the X-ray detector 151 before and after its movement.

Next, as shown in FIG. 10, the X-ray diagnosis apparatus 1 determines whether the movement of the X-ray tube 11 has been completed or not (Step S57). The process of determining whether the movement of the X-ray tube 11 has been completed or not is realized by the control function 21*f* in the processing circuit 21. Specifically, based on the movement amount of each of the plurality of movable directions of the X-ray tube 11 detected by the status detector 35 and the movement route acquired at Step S51, when the movement of the X-ray tube 11 has not been completed (Step S57: No), the X-ray diagnosis apparatus 1 returns to Step S53 described above and standbys, repeating the process from Step S53.

On the other hand, at Step S57, the X-ray diagnosis apparatus 1, based on the movement amount of each of the plurality of movable directions of the X-ray tube 11 detected by the status detector 35 and the movement route acquired at Step S51, when the movement of the X-ray tube 11 has been completed (Step S57: Yes), the X-ray diagnosis apparatus 1 outputs a completion of movement on the display 27 (Step S59). The process of outputting the completion of movement is realized by the output function 21*d* in the processing circuit 21.

Next, as shown in FIG. 10, the X-ray diagnosis apparatus 1 displays that the movement of the X-ray tube 11 has been completed (Step S61). The process of outputting the completion of movement is realized by the output function 21*d* in the processing circuit 21.

Specifically, the X-ray diagnosis apparatus 1 displays that the movement of the X-ray tube 11 has been completed to the operator via the display 27. For instance, the X-ray diagnosis apparatus 1 displays that the movement of the X-ray tube 11 has been completed on a pop-up screen. Note that the method of conveying to the operator that the movement of the X-ray tube 11 has been completed is not limited to this, but may be conveyed to the operator via other methods. That is to say, the method of conveying to the operator that the movement of the X-ray tube 11 has been completed is arbitrary, and for instance, at Step S61, when the output function 21d outputs on the speaker 29 that the movement of the X-ray tube 11 has been completed, the completion of the movement of the X-ray tube 11 may be output with voice, or at Step S61, when the output function 21d outputs to the printed circuit that the movement of the X-ray tube 11 has been completed, the completion of movement of the X-ray tube 11 may be printed out on a paper.

By the execution of Step S61, the locking control process according to the present embodiment ends.

Figure 11:
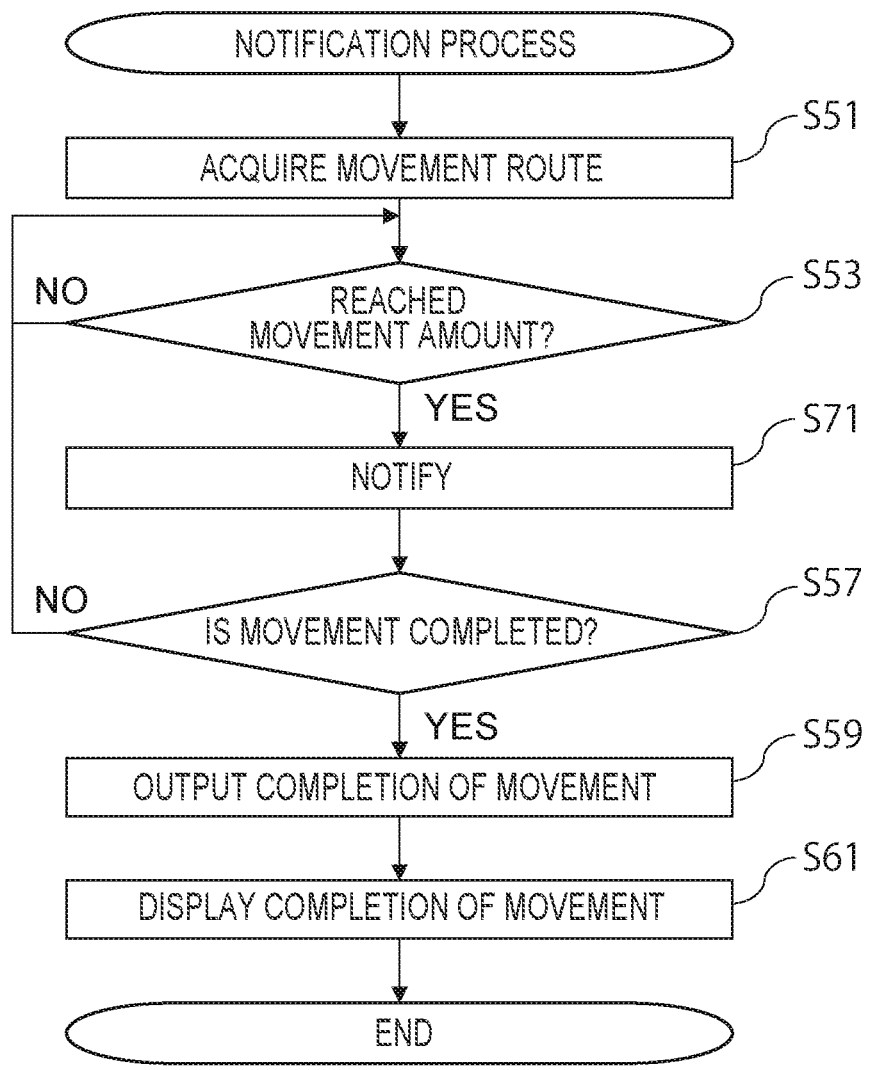
FIG. 11 is a flowchart explaining a content of a notification process executed in the X-ray diagnosis apparatus according to one embodiment.

Next, a notification process, executed by the X-ray diagnosis apparatus 1 according to the present embodiment, which notifies that it has reached the movement amount calculated by the calculation function 21b will be explained. FIG. 11 is a flowchart explaining a content of the notification process executed by the X-ray diagnosis apparatus 1 according to the present embodiment. Note that, since the processes of Step S51 and Step S53 before S71 shown in FIG. 11 are equivalent to the locking control process described above, description will be omitted.

Next, as shown in FIG. 11, based on the movement amount of each of the plurality of movable directions of the X-ray tube 11 detected by the status detector 35 and the movement route acquired at Step S51, when the movement of the X-ray tube 11 has reached the movement amount of the movement route acquired at Step S51 (Step S53: Yes), the X-ray diagnosis apparatus 1 notifies that the movement of the X-ray tube 11 has reached the movement amount of the movement route acquired at Step S51 (Step S71). The process of notifying that it has reached the movement is realized by the notification function 21g in the processing circuit 21.

Specifically, the X-ray diagnosis apparatus 1, based on the movement amount of each of the plurality of movable directions of the X-ray tube 11 detected by the status detector 35 and the movement route acquired at Step S51, notifies the operator that the movement of the X-ray tube 11 has reached the movement amount of the movement route acquired at Step S51. More specifically, for instance, when notifying using the display 27, the X-ray diagnosis apparatus 1 may be made to notify reaching the movement amount by displaying on the pop-up screen, or when notifying to the operator using the speaker 29, the X-ray diagnosis apparatus 1 may be made to notify reaching the movement amount with voice.

Note that, since the processes of Step S57, Step S59, and Step S61 performed after S71 are equivalent to the locking control process described above, description will be omitted. Likewise, the notification process according to the present embodiment ends with the execution of Step S59.

Figure 12:
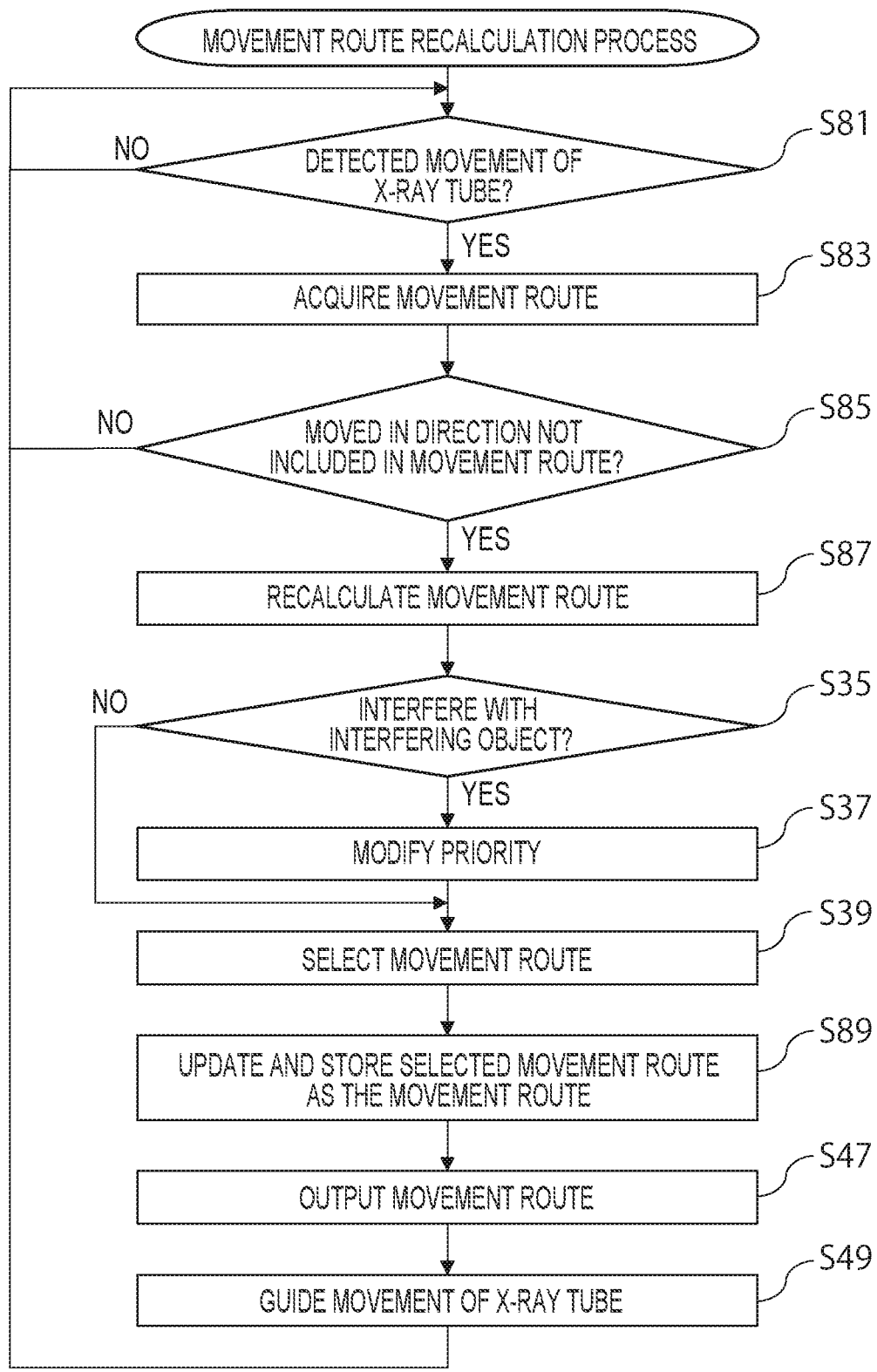
FIG. 12 is a flowchart explaining a content of a movement route recalculation process executed in the X-ray diagnosis apparatus according to one embodiment.

Next, when the X-ray tube 11 moves to a direction not included in the movement route, a movement route recalculation process, executed by the X-ray diagnosis apparatus 1 according to the present embodiment, that recalculates the movement route for the X-ray tube 11 to move from the relative positions of the X-ray tube 11 relative to the X-ray detector 151 to the irradiation positions 11b of the X-ray tube 11 will be explained. FIG. 12 is a flowchart explaining a content of the movement route recalculation process executed by the X-ray diagnosis apparatus 1 according to the present embodiment. For instance, the movement route recalculation process is a process executed when the detection member 39 detects the movement of the X-ray tube 11.

As shown in FIG. 12, first, the X-ray diagnosis apparatus 1 determines whether it has detected the movement of the X-ray tube 11 (Step S81). The process of determining whether it has determined the movement of the X-ray tube 11 is realized by the determination function 21c in the processing circuit 21. Specifically, based on the output of the detection member 39, when the X-ray diagnosis apparatus 1 has not detected the movement of the X-ray tube 11 (Step S81: No), the X-ray diagnosis apparatus 1 returns to Step S81 and standbys, repeating the process of Step S81.

On the other hand, at Step S71, based on the output of the detection member 39, when it has detected the movement of the X-ray tube 11 (Step S81: Yes), the X-ray diagnosis apparatus 1 acquires the movement route stored in the memory circuit 31 (Step S83). The process of acquiring the movement route stored in the memory circuit 31 is realized by the determination function 21c in the processing circuit 21. Specifically, the X-ray diagnosis apparatus 1 acquires the movement route stored at Step S45 of the movement route output process from the memory circuit 31.

Note that the X-ray diagnosis apparatus 1 uses the detection member 39 to detect the movement of the X-ray tube 11, but a method of detecting the movement of the X-ray tube 11 is not limited to this. That is to say, the method of detecting the movement of the X-ray tube 11 is arbitrary, for instance, the X-ray diagnosis apparatus 1 may use the status detector 35 to detect the movement of the X-ray tube 11. Likewise, for instance, the X-ray diagnosis apparatus 1 may detect the movement of the X-ray tube 11 based on the image imaged by the imager 17.

Next, as shown in FIG. 12, the X-ray diagnosis apparatus 1 determines whether the movement of the X-ray tube 11 detected by the detection member 39 is a movement in a direction not included in the movement route (Step S85). The process of determining whether it is the movement in the direction not included in the movement route is realized by the determination function 21c in the processing circuit 21. Specifically, the X-ray diagnosis apparatus 1, based on the movement route acquired in Step S83, when the movement of the X-ray tube 11 detected by the detection member 39 is not the movement in the direction not included in the movement route (Step S85: No), returns to Step S81 and standbys, repeating the process from Step S81. Here, the direction not included in the movement route indicates a direction for which the movement amount is not calculated for the movement route, which, for instance, in the example of FIG. 9, in route 1, is the direction which the arm rotation or the body movement is not included in the movement route.

On the other hand, at Step S85, based on the movement route acquired at Step S83, when the movement of the X-ray tube 11 detected by the detection member 39 is the movement in a direction not included in the movement route (Step S85: Yes), the X-ray diagnosis apparatus 1 recalculates the movement route for the X-ray tube 11 to move from the relative positions of the X-ray tube 11 relative to the X-ray detector 151 to the irradiation positions 11b of the X-ray tube 11 (Step S87). The process of recalculating the movement route is realized by the calculation function 21b in the processing circuit 21.

Specifically, the X-ray diagnosis apparatus 1, based on the feature member 153 shown on the image reimaged by the imager 17, recalculates the movement route for the X-ray tube 11 to move from the relative positions of the X-ray tube 11 relative to the X-ray detector 151 to the irradiation positions 11b of the X-ray tube 11. Since the process from Step S35 to Step S39 after Step 87 are equivalent to the movement route output process described above, description will be omitted. Note that, when only one movement route is calculated at Step S87, Step S35 to Step S39 may be omitted.

Next, as shown in FIG. 12, the X-ray diagnosis apparatus 1 updates the movement route stored in the memory circuit 31 with the selected movement route and stores it (Step S89). The process of updating and storing the selected movement route is realized by the calculation function 21b in the processing circuit 21. Specifically, the X-ray diagnosis apparatus 1 updates the movement route stored in the memory circuit 31 with the movement route selected at Step S39 of the movement route recalculation. Then, the X-ray diagnosis apparatus 1 stores the updated movement route in the memory circuit 31. Since the processes of Step S47 and Step S49 after Step S89 are equivalent to the movement route output process described above, description will be omitted.

The movement route recalculation process according to the present embodiment shown in FIG. 12 is repeatedly executed while the operator performs the movement of the X-ray tube 11, and ends when the operator ends the movement of the X-ray tube 11.

As described above, in the X-ray diagnosis apparatus 1 according to the present embodiment, since the X-ray diagnosis apparatus 1 is made to calculate the relative positions of the X-ray tube 11 relative to the X-ray detector 151 and the irradiation position 11b of the X-ray tube 11 that meets the X-ray imaging condition for which the relative positions of the X-ray tube 11 are predetermined, based on the relative positions of the X-ray tube 11 relative to the X-ray detector 151 and the irradiation position 11b of the X-ray tube 11 that meets the X-ray imaging condition for which the relative positions of the X-ray tube 11 are predetermined, calculate the movement route indicating the movement direction and the movement amount, output the calculated movement route, and guide the movement of the X-ray tube 11, the operator may easily perform an alignment to get an appropriate setting of the X-ray irradiation field relative to the X-ray detection surface of the X-ray detector 151. That is to say, since it is possible to confirm the movement route to move to the irradiation position of the X-ray tube 11, the operator may move the X-ray tube 11 to an appropriate position relative to the X-ray detector 151 and perform X-ray imaging.

Likewise, since the X-ray diagnosis apparatus 1, based on the movement amount of each of the plurality of movable directions of the X-ray tube 11 detected by the status detector 35 and the movement route calculated by the calculation function 21b, is made to lock the movement of the X-ray tube 11 in the direction which has reached the movement amount of each of the plurality of movable directions of the X-ray tube 11, the operator may move the X-ray tube 11 to the appropriate position relative to the X-ray detector 151 and perform X-ray imaging. Furthermore, since the X-ray diagnosis apparatus 1, based on the movement amount of each of the plurality of movable directions of the X-ray tube 11 detected by the status detector 35 and the movement route calculated by the calculation function 21b, is made to notify the operator via the display 27 or the speaker 29, the operator may easily notice that the X-ray tube 11 has been moved to the appropriate position relative to the X-ray detector 151.

Likewise, since the X-ray diagnosis apparatus 1, when the X-ray tube 11 moves to the direction not included in the movement route, is made to recalculate the movement route for the X-ray tube 11 to move from the relative positions of the X-ray tube 11 relative to the X-ray detector 151 to the irradiation position 11b of the X-ray tube 11, even when the operator considers a surrounding environment etc. and changes the movement route by the operator oneself, the operator may move the X-ray tube 11 to the appropriate position relative to the X-ray detector 151 and performs X-ray imaging.

Modified Example

The X-ray diagnosis apparatus 1 according to a modified example of the present embodiment described above may comprise a driver to move the X-ray tube 11 to the irradiation position of the X-ray tube 11, and the control function 21f, based on the movement route output by the output function 21d, by controlling the driver, may control the support member 19 to move the X-ray tube 11 to the irradiation position of the X-ray tube 11. Hereinafter, different parts from that of the present embodiment described above will be explained.

Figure 13:
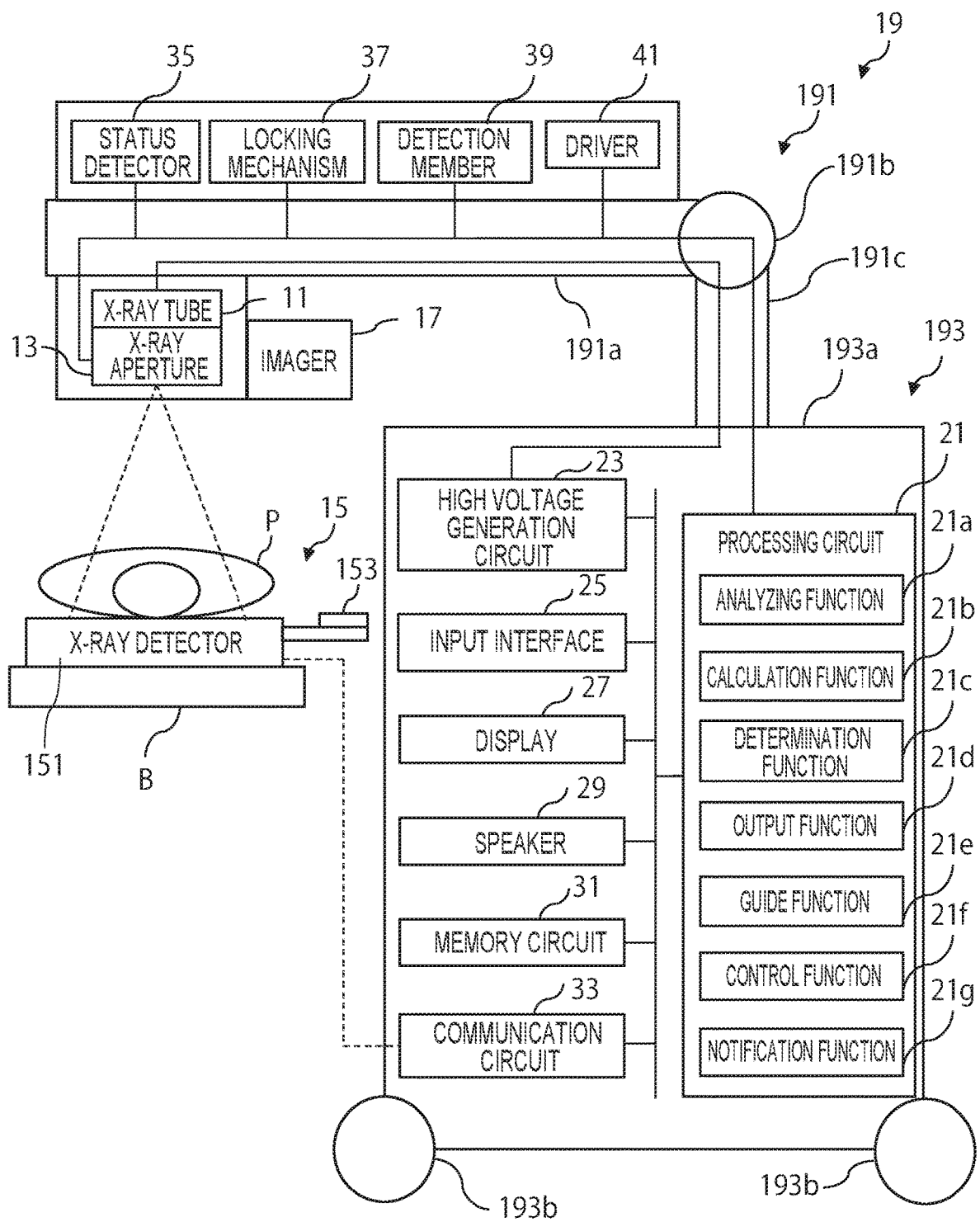
FIG. 13 is a block diagram illustrating the configuration example of the X-ray diagnosis apparatus according to a modified example.

FIG. 13 is a block diagram illustrating a configuration example of the X-ray diagnosis apparatus 1 according to the modified example, corresponding to FIG. 2 of the present embodiment described above. As shown in FIG. 13, the X-ray diagnosis apparatus 1 according to the modified example is configured by adding a driver 41 to the X-ray diagnosis apparatus 1 according to the present embodiment.

The driver 41 reads a drive signal from the processing circuit 21 and extends and contracts, vertically moves, rotates, or moves the support member 19. The driver 41, for instance, is configured by the motor or a linear actuator etc. Note that, in the example shown in FIG. 13, the driver 41 is mounted on the first arm 191a, but the place to provide the driver 41 is not limited to this. The driver 41 may be provided on the second arm 191b, the joint member 191c, or the support body member 193. Furthermore, the driver 41 is not limited to being provided on one place but may be provided on the plurality of places. That is to say, a number of the driver 41 is arbitrary, and is sufficient when it is provided on at least one place on the support member 19.

As described above, since the X-ray diagnosis apparatus 1 according to the modified example, based on the movement route, by the control function 21f controlling the driver 41, moves the X-ray tube 11 from the relative positions of the X-ray tube 11 relative to the X-ray detector 151 to the irradiation positions 11b of the X-ray tube 11, the X-ray diagnosis apparatus 1 may easily perform an alignment. That is to say, the X-ray diagnosis apparatus 1 may move the X-ray tube 11 to the appropriate position and perform X-ray imaging without having the operator operate the support member 19.

Likewise, the X-ray diagnosis apparatus 1 according to the present embodiment described above, by image analyzing an image which the X-ray detector 151 is imaged, may identify the position 151a of the X-ray detector 151. That is to say, the X-ray detector 151 may be made as the identifier according to the present embodiment. In this case, the feature member 153 may be omitted from the X-ray detection unit 15. When the feature member 153 is omitted from the X-ray detection unit 15, Step S15 and Step S17 are also omitted from the movement route output process. That is to say, when the X-ray diagnosis apparatus 1 analyzes the image imaged by the imager 17 at Step S13 and identifies the X-ray detector 151 in the image, the position 151a of the X-ray detector 151 may be acquired from the X-ray detector 151 identified at Step S19.

Also, the X-ray diagnosis apparatus 1 according to the present embodiment described above may output, by the output function 21d, information about at least one of the relative positions of the X-ray tube 11 relative to the X-ray detector 151 and the irradiation positions 11b of the X-ray tube 11. The relative positions of the X-ray tube 11 relative to the X-ray detector 151, for instance, is position information such as a current position of the X-ray tube 11 relative to the X-ray detector 151, and the information about the irradiation position 11*b* of the X-ray tube 11 is position information about a target position of the X-ray tube 11. The X-ray diagnosis apparatus 1 may display on the display 27 or output with voice by the speaker 29, to the operator, the information about at least one of the relative positions of the X-ray tube 11 relative to the X-ray detector 151 and the irradiation positions 11*b* of the X-ray tube 11.

Likewise, in the movement route output process of FIG. 3 described above, the output function 21*d* in the processing circuit 21, at Step S47, may output the movement amount and the movement direction from the relative positions of the X-ray tube 11 relative to the X-ray detector 151 calculated at Step S33 to the irradiation position 11*b* of the X-ray tube 11 as the movement route. In this case, Step S35 through Step S43 may be omitted from the movement route output process.

Likewise, the X-ray diagnosis apparatus 1 according to the present embodiment described above, when the X-ray tube 11 is moved, may output a rest of the operation necessary to move from the relative positions of the X-ray tube 11 relative to the X-ray detector 151 after its movement to the irradiation position 11*b* of the X-ray tube 11. In this case, the X-ray diagnosis apparatus 1, based on the feature member 153 shown on the image imaged by the imager 17, recalculates the movement amount of each of the plurality of directions from the relative positions to the irradiation position 11*b* and outputs the recalculated movement amount of each of the plurality of directions of the X-ray tube 11 from the relative positions to the irradiation position 11*b*.

That is to say, the X-ray diagnosis apparatus 1, based on the feature member 153 shown on the image imaged before the movement of the X-ray tube 11, calculates the relative positions of the X-ray tube 11 relative to the feature member 153 before its movement, and after the movement of the X-ray tube 11, the X-ray diagnosis apparatus 1, based on the feature member 153 shown on the image imaged after the movement of the X-ray tube 11, calculates the relative positions of the X-ray tube 11 relative to the feature member 153 after its movement, based on the difference of relative positions of the X-ray tube 11 relative to the feature member 153 before and after its movement, acquires the movement amount of each of the plurality of movable directions of the X-ray tube 11, recalculates the movement amount of each of the plurality of directions from the relative positions to the irradiation position 11*b*, and outputs the recalculated movement amount of each of the plurality of directions of the X-ray tube 11 from the relative positions to the irradiation position 11*b*.

Note that the X-ray diagnosis apparatus 1 has recalculated the movement of each of the plurality of directions from the relative positions to the irradiation position 11*b* based on the feature member 153 shown on the images imaged by the imager 17, but the movement amount of each of the plurality of directions from the relative positions to the irradiation positions may be recalculated based on the X-ray detector 151 shown on the image imaged by the imager or by other feature points. Furthermore, the movement amount of each of the plurality of directions from the relative positions to the irradiation position 11*b* may be recalculated based on the detections of the status detector 35.

Note that the word "processor" used in above descriptions means circuits such as, for example, a Central Processing Unit (CPU), a Graphics Processing Unit (GPU), an Application Specific Integrated Circuit (ASIC), a programmable logic device (for example, a Simple Programmable Logic Apparatus (SPLD), a Complex Programmable Logic Apparatus (CPLD), and a Field Programmable Gate Array (FPGA)). The processor executes functions by reading and executing programs stored in the memory. Note that programs may be configured to be directly integrated in the processor instead of being storing in the memory. In this case, the processor realizes functions by reading and executing programs stored in the circuit. Note that the processor is not limited to the case arranged as a single processor circuit, but may be configured as a single processor by combining a plurality of independent circuits to realize functions. Furthermore, a plurality of component elements in FIG. 3 may be integrated into one processor to realize the functions.

While certain embodiments have been described, these embodiments have been presented by way of example only and are not intended to limit the scope of the inventions. The embodiments may be in a variety of other forms. Furthermore, various omissions, substitutions and changes may be made without departing from the spirit of the inventions. The embodiments and their modifications are included in the scope and the subject matter of the invention, and at the same time included in the scope of the claimed inventions and their equivalents.

The invention claimed is:

1. An X-ray diagnosis apparatus, comprising:
an X-ray irradiator configured to irradiate X-rays;
an imager configured to image an identifier that identifies a position of an X-ray detector which detects X-rays;
a support member configured to support the X-ray irradiator to be movable in a plurality of directions; and
processing circuitry configured to
calculate, based on the identifier shown on an image imaged by the imager, a relative position of the X-ray irradiator relative to the X-ray detector and an irradiation position of the X-ray irradiator that meets the X-ray imaging condition for which the relative position of the X-ray tube is predetermined;
calculate a plurality of movement routes including a movement amount in each of the plurality of directions from the relative positions to the irradiation positions;
select, based on a priority of each of the preset plurality of directions, one movement route from the plurality of movement routes;
output, the selected one movement route as movement information indicating the movement amount and a movement direction of the X-ray irradiator from the relative position to the irradiation position; and
control, based on the output movement information, the support member to move the X-ray irradiator to the irradiation position.

2. The X-ray diagnosis apparatus of claim 1, wherein the processing circuitry is further configured to control the support member to move the X-ray irradiator based on the movement amount in each of the plurality of directions.

3. The X-ray diagnosis apparatus of claim 2,
wherein the support member is further configured to receive a movement operation in each of the plurality of directions; and
wherein the processing circuitry is further configured to control the support member to lock the movement of the X-ray irradiator in a direction which has reached a calculated movement amount.

4. The X-ray diagnosis apparatus of claim 3, wherein the processing circuitry is further configured to, based on the output movement information, guide a movement of the X-ray irradiator.

5. The X-ray diagnosis apparatus of claim 1, wherein the processing circuitry is further configured to,
when the X-ray irradiator moves to a direction not included in the selected movement route, based on the moving direction of the support member, recalculate a movement route including the movement amount in each of the plurality of directions from the relative positions to the irradiation positions.

6. The X-ray diagnosis apparatus of claim 1, wherein the processing circuitry is further configured to,
when the X-ray irradiator is moved, based on the identifier shown on the image imaged by the imager, recalculate the movement amount in each of the plurality of directions from the relative positions to the irradiation positions; and
output the recalculated movement amount in each of the plurality of directions of the X-ray irradiator from the relative positions to the irradiation positions.

7. The X-ray diagnosis apparatus of claim 1, wherein the processing circuitry is further configured to output information about at least one of the relative positions of the X-ray irradiator and the irradiation position of the X-ray irradiator.

8. The X-ray diagnosis apparatus of claim 1, wherein the processing circuitry is further configured to, with a position of the imager as a reference, calculate the relative position and the irradiation position.

9. The X-ray diagnosis apparatus of claim 3, wherein the processing circuitry is further configured to notify reaching of the calculated movement amount.

10. A non-transitory computer readable storage medium, which stores a program that causes a computer to execute processing comprising:
imaging an identifier that identifies a position of an X-ray detector which detects X-rays;
calculating, based on the identifier shown on an imaged image, a relative position of an X-ray irradiator that irradiates X-rays relative to the X-ray detector and an irradiation position of the X-ray detector that meets the X-ray imaging condition for which the relative position of the X-ray tube is predetermined;
calculating a plurality of movement routes including a movement amount in each of the plurality of directions from the relative positions to the irradiation positions,
selecting, based on a priority of each of the preset plurality of directions, one movement route from the plurality of movement routes,
outputting, the selected one movement route as movement information indicating the movement amount and a movement direction of the X-ray irradiator from the relative position to the irradiation position; and
controlling, based on the output movement information, the support member to move the X-ray irradiator to the irradiation position.

* * * * *